US009310368B1

(12) United States Patent
He et al.

(10) Patent No.: US 9,310,368 B1
(45) Date of Patent: Apr. 12, 2016

(54) HIGH AFFINITY MONOCLONAL ANTIBODIES FOR DETECTION OF SHIGA TOXIN 2 (STX2)

(71) Applicant: The United States of America, as represented by the Secretary of Agriculture, Washington, DC (US)

(72) Inventors: Xiaohua He, Richmond, CA (US); Larry H. Stanker, Livermore, CA (US); Luisa W. Cheng, San Francisco, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/039,439

(22) Filed: Sep. 27, 2013

Related U.S. Application Data

(60) Provisional application No. 61/707,821, filed on Sep. 28, 2012.

(51) Int. Cl.
| | |
|---|---|
| *C07K 16/12* | (2006.01) |
| *G01N 33/577* | (2006.01) |
| *G01N 33/53* | (2006.01) |
| *G01N 33/50* | (2006.01) |
| *G01N 33/569* | (2006.01) |

(52) U.S. Cl.
CPC ...... *G01N 33/56916* (2013.01); *C07K 16/1232* (2013.01); *G01N 2333/245* (2013.01)

(58) Field of Classification Search
None
See application file for complete search history.

(56) References Cited

U.S. PATENT DOCUMENTS

| | | | | |
|---|---|---|---|---|
| 8,846,058 | B2 * | 9/2014 | Smith et al. | 424/236.1 |
| 8,969,529 | B2 * | 3/2015 | O'Brien et al. | 530/387.9 |
| 9,145,455 | B2 * | 9/2015 | Stanker et al. | C07K 16/1282 435/7.32 |
| 2003/0215814 | A1 * | 11/2003 | Cockerill et al. | 435/6 |
| 2005/0282194 | A1 * | 12/2005 | Cockerill et al. | 435/6 |
| 2008/0038262 | A1 * | 2/2008 | Tzipori et al. | 424/133.1 |
| 2010/0298238 | A1 * | 11/2010 | Tumer et al. | 514/21.2 |
| 2011/0318357 | A1 * | 12/2011 | O'Brien et al. | 424/139.1 |
| 2015/0031557 | A1 * | 1/2015 | Tyler | 506/2 |

OTHER PUBLICATIONS

X. He et al. / Journal of Immunological Methods 389 (2013) 18-28.*
Jiao Y, Legge FS, Zeng X, Treutlein HR, Zeng J (2014) Antibody Recognition of Shiga Toxins (Stxs): Computational Identification of the Epitopes of Stx2 Subunit A to the Antibodies 11E10 and S2C4. PLoS One 9(2): e88191. doi:10.1371/journal.pone.0088191.*
Skinner et al, PLoS One, 2013, 8/9:e76563. doi:10.1371/journal.pone.0076563.*
He et al, Toxins 2012, 4, 487-504; doi:10.3390/toxins4070487.*
He et al, Applied and Environmental Microbiology, Jun. 2011, p. 3558-3564 vol. 77, No. 11.*
He et al, J. Agric. Food Chem. 2009, 57, 5084-5088.*
He X, Patfield S, Hnasko R, Rasooly R, Mandrell RE (2013) A Polyclonal Antibody Based Immunoassay Detects Seven Subtypes of Shiga Toxin 2 Produced by *Escherichia coli* in Human and Environmental Samples. PLoS One 8(10): e76368. doi:10.1371/journal.pone.0076368.*
Oloomi et al, Iran J. Allergy Asthma Immunol., Mar. 2011, 10/1:41-46.*
He et al, Method for Detecting Shiga-like Toxin-II in Bacterial Culture, ASM 109th General Meeting, May 2009, Abstract #Z102.*
Skinner C, McMahon S, Rasooly R, Carter JM, He X (2013) Purification and Characterization of Shiga Toxin 2f, an Immunologically Unrelated Subtype of Shiga Toxin 2. PLoS ONE 8(3): e59760. doi:10.1371/journal.pone.0059760.*
Greenspan et al, Nature Biotechnology 17:936-937, 1999.*
Greenbaum et al, Journal of Molecular Recognition, 20(2):75-82, 2007.*
Herbert, Dictionary of Immunology 4th Ed, Academic Press, 1995 pp. 58-59.*
Schmidt et al, Applied and Environmental Microbiology, Mar. 2000, p. 1205-1208 vol. 66, No. 3.*

* cited by examiner

*Primary Examiner* — Nita M Minnifield
(74) *Attorney, Agent, or Firm* — John D. Fado; Mark D. McNemar

(57) ABSTRACT

High affinity monoclonal antibodies against Stx2 and hybridomas that produce such antibodies are described. The antibodies may be used in a kit for detecting Stx2 and variants thereof in a sample as well as neutralization of Shiga toxin in vivo.

6 Claims, 12 Drawing Sheets

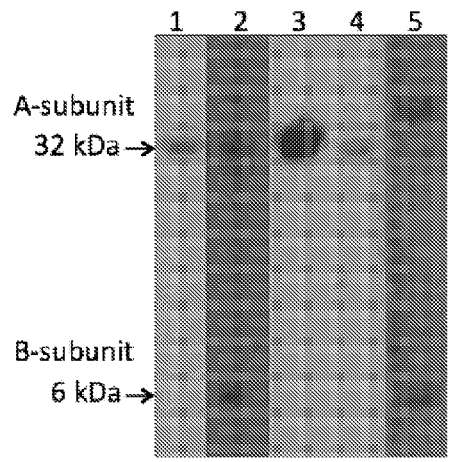 
FIG. 2A    FIG. 2B
FIG. 2

SEQUENCE LISTING

<160> NUMBER OF SEQ ID NOS: 32

<210> SEQ ID NO 1
<211> LENGTH: 339
<212> TYPE: PRT
<213> ORGANISM: Escherichia coli

<400> SEQUENCE: 1

```
Gly Ala Gly Cys Thr Cys Gly Ala Cys Ala Thr Thr Gly Thr Gly Cys
1               5                   10                  15

Thr Gly Ala Cys Cys Ala Gly Ala Cys Thr Cys Cys Ala Ala
            20                  25                  30

Ala Thr Thr Cys Cys Thr Gly Cys Thr Thr Gly Thr Ala Thr Cys Ala
            35                  40                  45

Gly Cys Ala Gly Gly Ala Gly Ala Cys Ala Gly Gly Thr Thr Ala
        50                  55                  60

Cys Cys Ala Thr Ala Ala Cys Cys Thr Gly Cys Ala Ala Gly Gly Cys
65                  70                  75                  80

Cys Ala Gly Thr Cys Ala Gly Ala Gly Thr Gly Thr Ala Gly Thr
            85                  90                  95

Ala Ala Thr Gly Thr Thr Gly Thr Ala Gly Cys Thr Thr Gly Gly Thr
            100                 105                 110

Ala Cys Cys Ala Ala Cys Ala Gly Ala Ala Gly Cys Cys Ala Gly Gly
        115                 120                 125

Gly Cys Ala Gly Thr Cys Thr Cys Cys Thr Ala Ala Ala Cys Thr Gly
        130                 135                 140

Cys Thr Gly Ala Thr Ala Thr Ala Cys Thr Ala Thr Gly Cys Ala Thr
145                 150                 155                 160

Cys Cys Ala Ala Thr Cys Gly Cys Thr Ala Cys Ala Cys Thr Gly Gly
                165                 170                 175

Ala Gly Thr Cys Cys Cys Thr Gly Ala Thr Cys Gly Cys Thr Thr Cys
            180                 185                 190

Ala Cys Thr Gly Gly Cys Ala Gly Thr Gly Gly Ala Thr Ala Thr Gly
        195                 200                 205

Gly Gly Ala Cys Gly Gly Ala Thr Thr Thr Cys Ala Cys Thr Thr Thr
        210                 215                 220

Cys Ala Cys Cys Ala Thr Cys Ala Gly Cys Ala Cys Thr Gly Thr Gly
225                 230                 235                 240

Cys Ala Gly Gly Cys Thr Gly Ala Ala Gly Ala Cys Cys Thr Gly Gly
            245                 250                 255

Cys Ala Gly Thr Thr Thr Ala Thr Thr Thr Cys Thr Gly Thr Cys Ala
                260                 265                 270

Gly Cys Ala Gly Gly Ala Gly Thr Ala Thr Ala Gly Cys Thr Cys Thr
            275                 280                 285
```

```
Ala Cys Gly Thr Gly Gly Ala Cys Gly Thr Cys Gly Gly Thr Gly
            290                 295                 300

Gly Ala Gly Gly Cys Ala Cys Cys Ala Ala Gly Cys Thr Gly Gly Ala
305                 310                 315                 320

Ala Ala Thr Cys Ala Ala Ala Cys Gly Gly Gly Cys Thr Gly Ala Thr
                325                 330                 335

Gly Cys Thr

<210> SEQ ID NO 2
<211> LENGTH: 339
<212> TYPE: PRT
<213> ORGANISM: Escherichia coli

<400> SEQUENCE: 2

Gly Ala Gly Cys Thr Cys Gly Ala Cys Ala Thr Thr Gly Thr Gly Ala
1               5                   10                  15

Thr Gly Ala Cys Cys Cys Ala Gly Thr Cys Thr Cys Cys Ala Thr Cys
                20                  25                  30

Cys Thr Cys Cys Thr Thr Ala Ala Cys Thr Gly Cys Cys Thr Cys Thr
            35                  40                  45

Cys Thr Gly Gly Gly Ala Gly Ala Ala Gly Gly Ala Gly Thr Cys Ala
50                  55                  60

Gly Thr Cys Thr Cys Ala Cys Thr Thr Gly Thr Cys Gly Gly Ala Cys
65                  70                  75                  80

Ala Ala Gly Thr Cys Ala Gly Gly Ala Ala Thr Thr Ala Gly Gly Thr
                85                  90                  95

Gly Gly Thr Thr Ala Cys Cys Thr Ala Ala Gly Cys Thr Gly Gly Cys
                100                 105                 110

Thr Thr Cys Ala Gly Cys Ala Gly Ala Ala Cys Cys Ala Gly Gly Ala
            115                 120                 125

Thr Gly Gly Ala Ala Cys Thr Ala Thr Ala Ala Ala Cys Gly Gly Cys
            130                 135                 140

Cys Thr Gly Ala Thr Cys Thr Ala Cys Gly Cys Cys Gly Cys Ala Thr
145                 150                 155                 160

Cys Cys Ala Cys Thr Thr Thr Ala Gly Ala Thr Cys Thr Gly Gly Gly
                165                 170                 175

Thr Gly Thr Cys Cys Cys Ala Ala Ala Ala Gly Gly Thr Thr Cys Ala
            180                 185                 190

Gly Thr Gly Gly Cys Ala Gly Thr Gly Gly Thr Cys Thr Gly
            195                 200                 205

Gly Gly Thr Cys Ala Gly Ala Thr Thr Ala Thr Thr Cys Thr Cys Thr
            210                 215                 220

Cys Ala Cys Cys Ala Thr Cys Ala Gly Cys Ala Gly Cys Cys Thr Thr
225                 230                 235                 240

Gly Ala Gly Thr Cys Thr Gly Ala Ala Gly Ala Thr Thr Thr Thr Gly
                245                 250                 255

Cys Ala Gly Ala Cys Thr Ala Thr Thr Ala Cys Thr Gly Cys Thr Thr
            260                 265                 270

Ala Cys Ala Ala Thr Ala Thr Gly Cys Thr Ala Gly Thr Thr Ala Thr
                275                 280                 285

Cys Cys Thr Cys Cys Gly Ala Cys Gly Thr Cys Gly Gly Thr Gly Gly
            290                 295                 300

Gly Ala Gly Gly Cys Ala Cys Cys Ala Ala Gly Cys Thr Gly Gly Ala
305                 310                 315                 320
```

Ala Ala Thr Cys Ala Ala Cys Gly Gly Cys Thr Ala Thr
            325                 330                 335

Gly Cys Thr

<210> SEQ ID NO 3
<211> LENGTH: 339
<212> TYPE: PRT
<213> ORGANISM: Escherichia coli

<400> SEQUENCE: 3

Gly Ala Gly Cys Thr Cys Gly Ala Thr Ala Thr Gly Thr Gly Cys
1               5                   10                  15

Thr Gly Ala Cys Ala Cys Ala Gly Ala Cys Thr Cys Ala Gly Cys
                20                  25                  30

Cys Ala Thr Cys Thr Thr Gly Thr Cys Thr Gly Thr Gly Ala Gly Thr
                35                  40                  45

Cys Cys Ala Gly Gly Ala Gly Ala Ala Ala Gly Cys Gly Thr Cys Ala
                50                  55                  60

Gly Thr Thr Thr Cys Thr Cys Cys Thr Gly Cys Ala Gly Gly Gly Cys
65                  70                  75                  80

Cys Ala Gly Thr Cys Ala Gly Ala Ala Cys Ala Thr Thr Gly Gly Cys
                85                  90                  95

Ala Cys Ala Gly Ala Cys Ala Thr Ala Cys Ala Gly Thr Gly Gly Thr
                100                 105                 110

Ala Thr Cys Ala Gly Cys Ala Ala Gly Ala Ala Cys Ala Ala Ala
                115                 120                 125

Thr Gly Gly Thr Thr Cys Thr Cys Ala Ala Gly Gly Cys Thr Thr
                130                 135                 140

Cys Thr Cys Ala Thr Ala Ala Gly Thr Ala Thr Gly Cys Thr Thr
145                 150                 155                 160

Cys Thr Gly Ala Gly Thr Cys Thr Ala Thr Cys Thr Cys Thr Gly Gly
                165                 170                 175

Gly Ala Thr Cys Cys Cys Thr Thr Cys Cys Ala Gly Gly Thr Thr Thr
                180                 185                 190

Ala Gly Thr Gly Gly Cys Ala Gly Thr Gly Gly Ala Thr Cys Ala Gly
                195                 200                 205

Gly Gly Ala Cys Ala Gly Ala Thr Thr Thr Ala Cys Thr Cys Thr
                210                 215                 220

Thr Ala Gly Thr Ala Thr Cys Ala Ala Cys Ala Gly Thr Gly Thr Gly
225                 230                 235                 240

Gly Ala Ala Thr Cys Thr Gly Ala Ala Gly Ala Thr Gly Thr Thr Gly
                245                 250                 255

Cys Ala Gly Ala Thr Thr Ala Thr Thr Ala Cys Thr Gly Thr Cys Ala
                260                 265                 270

Ala Cys Ala Ala Ala Gly Thr Thr Ala Thr Ala Gly Cys Thr Gly Gly
                275                 280                 285

Cys Cys Ala Ala Cys Gly Ala Cys Gly Thr Thr Cys Gly Gly Thr Gly
                290                 295                 300

Gly Ala Gly Gly Cys Ala Cys Ala Ala Gly Cys Thr Gly Gly Ala
305                 310                 315                 320

Ala Ala Thr Cys Ala Gly Ala Cys Gly Gly Gly Cys Thr Gly Ala Thr
                325                 330                 335

Gly Cys Thr

<210> SEQ ID NO 4
<211> LENGTH: 333
<212> TYPE: PRT
<213> ORGANISM: Escherichia coli

<400> SEQUENCE: 4

```
Gly Ala Gly Cys Thr Cys Gly Ala Thr Thr Gly Thr Gly Ala
1               5                   10                  15

Thr Gly Ala Cys Cys Ala Ala Cys Thr Cys Ala Gly Cys
            20                  25                  30

Ala Ala Thr Cys Ala Thr Gly Thr Cys Thr Gly Cys Ala Cys Thr
                35                  40                  45

Cys Cys Ala Gly Gly Gly Ala Gly Ala Gly Gly Thr Cys Ala
    50                  55                  60

Cys Cys Ala Thr Gly Ala Cys Thr Gly Cys Ala Gly Thr Gly Cys
65                  70                  75                  80

Cys Ala Gly Cys Thr Cys Ala Ala Gly Thr Gly Thr Ala Ala Gly Thr
                85                  90                  95

Thr Ala Cys Ala Thr Gly Cys Ala Cys Thr Gly Gly Thr Ala Cys Cys
                100                 105                 110

Ala Gly Cys Ala Gly Ala Ala Gly Thr Cys Ala Gly Gly Cys Ala Cys
                115                 120                 125

Cys Thr Cys Cys Cys Ala Ala Ala Gly Ala Thr Gly Gly
    130                 135                 140

Ala Thr Thr Thr Ala Thr Gly Ala Cys Ala Cys Thr Cys Ala
145                 150                 155                 160

Ala Ala Cys Thr Gly Gly Cys Thr Thr Cys Thr Gly Ala Gly Thr
                165                 170                 175

Cys Cys Cys Thr Gly Cys Thr Cys Gly Cys Thr Thr Cys Ala Gly Thr
                180                 185                 190

Gly Gly Cys Ala Gly Thr Gly Gly Thr Cys Thr Gly Gly Gly Ala
            195                 200                 205

Cys Cys Thr Cys Thr Thr Ala Cys Thr Cys Thr Cys Thr Cys Ala Cys
    210                 215                 220

Ala Ala Thr Cys Ala Gly Cys Ala Cys Gly Thr Gly Gly Ala Cys
225                 230                 235                 240

Ala Cys Thr Gly Ala Ala Gly Ala Thr Gly Cys Thr Gly Cys Cys Ala
                245                 250                 255

Cys Thr Thr Ala Thr Ala Cys Thr Gly Cys Cys Ala Gly Cys Ala
    260                 265                 270

Gly Thr Gly Gly Ala Gly Thr Ala Gly Thr Ala Ala Cys Cys Cys Ala
            275                 280                 285

Ala Cys Gly Thr Thr Cys Gly Thr Gly Gly Gly Cys Ala
    290                 295                 300

Cys Cys Ala Ala Gly Cys Thr Gly Gly Ala Ala Ala Thr Cys Ala Ala
305                 310                 315                 320

Ala Cys Gly Gly Gly Cys Thr Gly Ala Thr Gly Cys Thr
                325                 330
```

<210> SEQ ID NO 5
<211> LENGTH: 339
<212> TYPE: PRT
<213> ORGANISM: Escherichia coli

<400> SEQUENCE: 5

```
Gly Ala Gly Cys Thr Cys Gly Ala Thr Thr Gly Thr Gly Cys
1               5                   10                  15
Thr Cys Ala Cys Ala Cys Ala Gly Ala Cys Thr Ala Cys Ala Gly Cys
            20                  25                  30
Cys Thr Cys Cys Cys Thr Ala Thr Cys Thr Gly Thr Ala Thr Cys Thr
            35                  40                  45
Gly Thr Gly Gly Gly Ala Gly Ala Ala Cys Thr Gly Thr Cys Ala
    50                  55                  60
Cys Cys Ala Thr Cys Ala Cys Ala Thr Gly Thr Cys Gly Ala Gly Cys
65                  70                  75                  80
Gly Ala Gly Thr Gly Ala Gly Ala Ala Thr Ala Thr Thr Thr Ala Cys
                85                  90                  95
Ala Gly Thr Ala Ala Thr Thr Thr Ala Gly Cys Ala Thr Gly Gly Thr
                100                 105                 110
Ala Thr Cys Ala Gly Cys Ala Gly Ala Ala Cys Ala Gly Gly Gly
            115                 120                 125
Ala Ala Ala Ala Thr Cys Thr Cys Thr Cys Ala Gly Cys Thr Cys
                130                 135                 140
Cys Thr Gly Gly Thr Cys Thr Ala Thr Gly Cys Thr Gly Cys Ala Ala
145                 150                 155                 160
Cys Ala Ala Ala Gly Thr Thr Ala Gly Cys Ala Gly Ala Thr Gly Gly
                165                 170                 175
Thr Gly Thr Gly Cys Cys Ala

```
Thr Gly Ala Gly Cys Thr Gly Thr Gly Ala Ala Cys Cys Thr
         35                  40                  45
Gly Gly Gly Gly Cys Cys Thr Cys Ala Gly Thr Gly Ala Gly Ala
 50                  55                  60
Thr Ala Thr Cys Cys Thr Gly Cys Ala Ala Gly Gly Cys Thr Cys
 65                  70                  75                  80
Thr Gly Gly Ala Thr Ala Cys Ala Cys Ala Thr Cys Ala Thr Thr
                 85                  90                  95
Gly Ala Cys Thr Ala Cys Ala Ala Ala Thr Gly Cys Ala Cys Thr
                100                 105                 110
Gly Gly Gly Thr Gly Ala Ala Gly Cys Ala Gly Ala Gly Cys Cys Ala
            115                 120                 125
Thr Gly Gly Ala Ala Ala Gly Ala Gly Cys Cys Thr Thr Gly Ala Gly
            130                 135                 140
Thr Gly Gly Ala Thr Thr Gly Gly Ala Thr Ala Thr Ala Thr Thr Thr
145                 150                 155                 160
Ala Thr Cys Cys Thr Thr Ala Cys Ala Ala Thr Gly Gly Thr Gly Gly
                165                 170                 175
Thr Ala Cys Thr Gly Gly Cys Thr Ala Thr Ala Ala Thr Cys Ala Gly
            180                 185                 190
Ala Ala Gly Thr Thr Cys Ala Ala Gly Ala Gly Cys Ala Ala Gly Gly
            195                 200                 205
Cys Cys Ala Cys Ala Thr Thr Gly Ala Cys Thr Gly Thr Ala Gly Ala
210                 215                 220
Cys Ala Ala Thr Cys Cys Thr Cys Ala Gly Cys Ala Cys Ala
225                 230                 235                 240
Gly Cys Cys Thr Ala Cys Ala Thr Gly Ala Gly Cys Thr Cys
                245                 250                 255
Gly Cys Ala Gly Cys Cys Thr Gly Ala Cys Ala Thr Cys Thr Gly Ala
            260                 265                 270
Gly Gly Ala Cys Thr Cys Thr Gly Cys Ala Gly Thr Cys Thr Ala Thr
            275                 280                 285
Thr Ala Cys Thr Gly Thr Gly Cys Ala Ala Gly Ala Gly Thr Cys Thr
290                 295                 300
Ala Thr Ala Gly Gly Thr Ala Cys Gly Cys Cys Thr Gly Gly Thr Thr
305                 310                 315                 320
Thr Gly Cys Thr Thr Ala Cys Thr Gly Gly Gly Cys Cys Ala Ala
            325                 330                 335
Gly Gly Gly Ala Cys Thr Cys Thr Gly Gly Thr Cys Ala Cys Thr Gly
            340                 345                 350
Thr Cys Thr Cys Thr Gly Cys Ala Gly Cys Cys Ala Ala Ala Cys
            355                 360                 365
Gly Ala Cys Ala Cys Cys Cys Cys Ala Thr Cys Thr Gly Thr Cys
            370                 375                 380
Thr Ala Thr Ala Gly Ala Thr Cys Thr Thr Cys Cys
385                 390                 395

<210> SEQ ID NO 7
<211> LENGTH: 366
<212> TYPE: PRT
<213> ORGANISM: Escherichia coli

<400> SEQUENCE: 7

Gly Ala Ala Thr Thr Cys Gly Ala Gly Gly Thr Cys Ala Ala Gly Cys
 1               5                  10                  15
```

Thr Gly Gly Ala Gly Ala Gly Thr Cys Thr Gly Ala Cys Cys
            20              25              30

Thr Gly Gly Cys Cys Thr Gly Thr Gly Gly Cys Gly Cys Cys
        35              40              45

Thr Cys Ala Cys Ala Gly Ala Gly Cys Cys Thr Thr Cys Cys Ala
    50              55              60

Thr Cys Ala Cys Ala Thr Gly Cys Ala Cys Cys Gly Thr Cys Thr Cys
65              70              75              80

Ala Gly Gly Gly Thr Thr Cys Thr Cys Ala Thr Ala Ala Gly Cys
            85              90              95

Gly Gly Cys Ala Ala Thr Ala Gly Thr Gly Thr Ala Ala Cys Thr
            100             105             110

Gly Gly Gly Thr Thr Cys Gly Cys Cys Ala Gly Cys Cys Ala Cys Cys
            115             120             125

Ala Gly Gly Ala Ala Gly Gly Gly Thr Cys Thr Gly Gly Ala Gly
            130             135             140

Thr Gly Gly Cys Thr Gly Gly Gly Cys Ala Thr Gly Ala Thr Ala Thr
145 150 155 160

Gly Gly Gly Gly Thr Gly Ala Thr Gly Gly Ala Ala Cys Cys Ala Cys
165 170 175

Ala Gly Ala Cys Thr Ala Thr Ala Ala Thr Thr Cys Ala Ala Cys Thr
180 185 190

Cys Thr Cys Ala Ala Ala Thr Cys Cys Ala Gly Ala Cys Thr Gly Ala
195 200 205

Gly Cys Ala Thr Cys Thr Gly Gly Ala Ala Gly Gly Ala Cys Ala Ala
210 215 220

Thr Thr Cys Cys Ala Ala Gly Ala Gly Cys Cys Ala Ala Gly Thr Thr
225 230 235 240

Cys Thr Cys Thr Thr Ala Ala Ala Ala Ala Thr Gly Ala Ala Cys Ala
245 250 255

Gly Thr Cys Thr Gly Cys Ala Ala Ala Cys Thr Gly Ala Thr Gly Ala
260 265 270

Cys Ala Cys Ala Gly Cys Cys Ala Gly Ala Thr Ala Cys Thr Ala Cys
275 280 285

Thr Gly Thr Gly Cys Cys Thr Thr Cys Cys Gly Ala Cys Ala Thr Thr
290 295 300

Ala Cys Thr Ala Cys Gly Gly Cys Ala Thr Cys Gly Gly Cys Thr Ala
305 310 315 320

Thr Gly Cys Thr Ala Thr Gly Gly Ala Cys Thr Ala Cys Thr Gly Gly
325 330 335

Gly Gly Lys Tyr Ala Ala Gly Gly Ala Ala Cys Cys Thr Cys Ala Cys
340 345 350

Thr Cys Ala Cys Cys Gly Thr Cys Thr Cys Cys Thr Cys Ala
355 360 365

<210> SEQ ID NO 8
<211> LENGTH: 380
<212> TYPE: PRT
<213> ORGANISM: Escherichia coli

<400> SEQUENCE: 8

Gly Ala Ala Thr Thr Cys Gly Ala Gly Gly Thr Cys Ala Ala Gly Cys
1 5 10 15

Thr Gly Gly Ala Gly Cys Ala Gly Thr Cys Thr Gly Gly Ala Gly Gly

```
            20                  25                  30
Ala Gly Ala Cys Thr Thr Ala Gly Thr Gly Ala Ala Gly Cys Cys Thr
        35                  40                  45

Gly Gly Ala Gly Gly Gly Thr Cys Cys Cys Thr Gly Ala Ala Ala Cys
    50                  55                  60

Thr Cys Thr Cys Cys Thr Gly Thr Gly Cys Ala Gly Cys Cys Thr Cys
65                  70                  75                  80

Thr Gly Gly Ala Thr Thr Cys Ala Cys Thr Thr Thr Cys Ala Gly Thr
                85                  90                  95

Ala Cys Thr Thr Ala Thr Gly Gly Cys Ala Thr Gly Thr Cys Thr Thr
            100                 105                 110

Gly Gly Gly Thr Thr Cys Gly Cys Cys Ala Gly Ala Cys Thr Cys Cys
        115                 120                 125

Ala Gly Ala Cys Ala Ala Gly Ala Ala Ala Cys Thr Gly Gly Ala Gly
    130                 135                 140

Thr Gly Gly Gly Thr Cys Gly Cys Ala Ala Cys Cys Ala Thr Thr Ala
145                 150                 155                 160

Gly Thr Thr Ala Thr Gly Gly Thr Thr Ala Thr Ala Cys Thr Thr Ala
                165                 170                 175
Cys Ala Cys Cys Thr Ala Cys Thr Ala Thr Cys Cys Ala Gly Ala Cys
            180                 185                 190

Ala Gly Thr Gly Thr Gly Ala Ala Gly Gly Gly Gly Cys Gly Ala Thr
        195                 200                 205

Thr Cys Ala Cys Cys Ala Thr Thr Thr Cys Cys Ala Gly Ala Gly Ala
    210                 215                 220

Cys Ala Ala Thr Gly Cys Cys Cys Ala Gly Ala Ala Cys Ala Cys Cys
225                 230                 235                 240

Cys Thr Gly Thr Ala Cys Cys Thr Ala Cys Ala Ala Ala Thr Gly Ala
                245                 250                 255

Gly Cys Ala Gly Thr Cys Thr Gly Ala Ala Cys Thr Cys Thr Gly Ala
            260                 265                 270

Gly Gly Ala Cys Ala Cys Ala Gly Cys Cys Ala Thr Gly Thr Ala Thr
        275                 280                 285

Thr Ala Cys Thr Gly Thr Gly Thr Ala Ala Gly Ala Cys Gly Gly Gly
    290                 295                 300

Ala Ala Gly Ala Thr Cys Ala Cys Gly Gly Gly Gly Cys Thr Ala Thr
305                 310                 315                 320

Gly Gly Ala Cys Thr Ala Cys Thr Gly Gly Gly Gly Thr Cys Ala Ala
                325                 330                 335

Gly Gly Ala Ala Cys Cys Thr Cys Ala Gly Thr Cys Ala Cys Cys Gly
            340                 345                 350

Thr Cys Thr Cys Cys Thr Cys Ala Gly Cys Cys Ala Ala Ala Ala Cys
        355                 360                 365

Gly Ala Cys Ala Cys Cys Cys Cys Cys Ala Thr Cys
    370                 375                 380
```

<210> SEQ ID NO 9
<211> LENGTH: 396
<212> TYPE: PRT
<213> ORGANISM: Escherichia coli

<400> SEQUENCE: 9

```
Gly Ala Ala Thr Thr Cys Gly Ala Ala Gly Thr Gly Ala Ala Gly Cys
1               5                   10                  15
```

```
Thr Gly Gly Ala Gly Ala Gly Thr Cys Ala Gly Gly Gly Cys
             20              25              30

Thr Gly Ala Ala Cys Thr Gly Cys Ala Ala Gly Ala Cys Cys Thr
         35              40              45

Gly Gly Gly Gly Cys Cys Thr Cys Ala Gly Thr Gly Ala Gly Ala
     50              55              60

Thr Gly Thr Cys Cys Thr Gly Cys Ala Ala Gly Gly Cys Thr Thr Cys
 65              70              75              80

Thr Gly Gly Cys Thr Ala Cys Ala Thr Cys Ala Cys Gly Ala Thr Gly
                 85              90              95

Cys Ala Cys Thr Gly Gly Ala Thr Ala Ala Ala Cys Ala Gly Ala
                 100             105             110

Gly Gly Cys Cys Thr Gly Gly Ala Cys Ala Gly Gly Thr Cys Thr
             115             120             125

Gly Gly Ala Ala Thr Gly Gly Ala Thr Thr Gly Gly Ala Thr Ala Cys
     130             135             140

Ala Thr Thr Ala Ala Thr Cys Cys Thr Ala Ala Cys Ala Gly Thr Gly
 145             150             155             160

Gly Thr Thr Ala Thr Ala Cys Thr Ala Ala Thr Thr Ala Cys Ala Ala
                 165             170             175

Thr Cys Ala Gly Ala Ala Gly Thr Thr Cys Ala Ala Gly Gly Ala Cys
                 180             185             190

Ala Ala Gly Gly Cys Cys Ala Cys Ala Ala Thr Gly Ala Cys Thr Gly
         195             200             205

Cys Gly G

```
Gly Ala Ala Thr Thr Cys Cys Ala Gly Gly Thr Gly Ala Ala Gly Cys
1               5                   10                  15

Thr Gly Cys Ala Gly Gly Ala Gly Thr Cys Thr Gly Gly Ala Cys Cys
            20                  25                  30

Thr Gly Ala Gly Cys Thr Gly Ala Ala Gly Ala Ala Gly Cys Cys Thr
        35                  40                  45

Gly Gly Ala Gly Ala Gly Ala Cys Ala Gly Thr Cys Ala Ala Gly Ala
    50                  55                  60

Thr Cys Thr Cys Cys Thr Gly Cys Ala Ala Gly Gly Cys Thr Thr Cys
65                  70                  75                  80

Thr Gly Gly Gly Thr Ala Thr Ala Cys Cys Thr Thr Cys Ala Cys Ala
                85                  90                  95

Ala Ala Cys Thr Ala Thr Gly Gly Ala Ala Thr Gly Ala Ala Cys Thr
            100                 105                 110

Gly Gly Gly Thr Gly Ala Ala Gly Cys Ala Gly Gly Cys Thr Cys Cys
        115                 120                 125

Ala Gly Gly Ala Ala Ala Gly Gly Gly Thr Thr Thr Ala Ala Ala Gly
    130                 135                 140

Thr Gly Gly Ala Thr Gly Gly Gly Cys Thr Gly Gly Ala Thr Thr Ala
145                 150                 155                 160

Cys Cys Ala Cys Cys Thr Ala Cys Ala Cys Thr Gly Gly Ala Gly Ala
                165                 170                 175

Gly Cys Cys Ala Ala Cys Ala Thr Ala Thr Gly Cys Thr Gly Ala Thr
            180                 185                 190

Gly Ala Cys Thr Thr Cys Ala Ala Gly Gly Gly Ala Cys Gly Gly Thr
        195                 200                 205

Thr Thr Gly Cys Cys Thr Thr Cys Thr Cys Thr Thr Thr Gly Gly Ala
    210                 215                 220

Ala Ala Cys Cys Thr Cys Thr Gly Cys Cys Ala Gly Cys Ala Cys Thr
225                 230                 235                 240

Gly Cys Cys Thr Ala Thr Thr Thr Gly Cys Ala Gly Ala Thr Cys Ala
                245                 250                 255

Ala Cys Ala Ala Cys Cys Thr Cys Ala Ala Ala Ala Ala Thr Gly Ala
            260                 265                 270

Gly Gly Ala Cys Thr Cys Gly Gly Cys Thr Ala Cys Ala Thr Ala Thr
        275                 280                 285

Thr Thr Cys Thr Gly Thr Gly Thr Thr Ala Gly Ala Thr Ala Thr Gly
    290                 295                 300

Gly Thr Ala Ala Cys Thr Thr Cys Ala Gly Ala Gly Gly Ala Thr Ala
305                 310                 315                 320

Cys Thr Thr Cys Gly Ala Thr Gly Thr Cys Thr Gly Gly Gly Gly Cys
                325                 330                 335

Gly Cys Ala Gly Gly Gly Ala Cys Cys Ala Cys Gly Gly Thr Cys Ala
            340                 345                 350

Cys Cys Gly Thr Cys Thr Cys Cys Thr Cys Ala Gly Cys Cys Ala Ala
        355                 360                 365

Ala Ala Cys Gly Ala Cys Ala Cys Cys Cys Cys Cys Ala Thr Cys Thr
    370                 375                 380

Gly Thr Cys Thr Ala Thr Ala Gly Ala Thr Cys Thr
385                 390                 395
```

<210> SEQ ID NO 11
<211> LENGTH: 33

```
<212> TYPE: PRT
<213> ORGANISM: Escherichia coli

<400> SEQUENCE: 11

Gly Gly Ala Ala Thr Thr Cys Cys Ala Thr Thr Gly Ala Ala Gly
1               5                   10                  15

Thr Gly Thr Ala Thr Ala Thr Thr Ala Thr Thr Thr Ala Ala Ala Thr
                20                  25                  30

Gly

<210> SEQ ID NO 12
<211> LENGTH: 20
<212> TYPE: PRT
<213> ORGANISM: Escherichia coli

<400> SEQUENCE: 12

Cys Gly Thr Ala Ala Gly Gly Cys Thr Thr Gly Thr Gly Cys Thr Gly
1               5                   10                  15

Thr Gly Ala Cys
                20

<210> SEQ ID NO 13
<211> LENGTH: 20
<212> TYPE: PRT
<213> ORGANISM: Escherichia coli

<400> SEQUENCE: 13

Gly Thr Cys Ala Cys Ala Gly Cys Ala Cys Ala Ala Gly Cys Cys Thr
1               5                   10                  15

Thr Ala Cys Gly
                20

<210> SEQ ID NO 14
<211> LENGTH: 38
<212> TYPE: PRT
<213> ORGANISM: Escherichia coli

<400> SEQUENCE: 14

Cys Cys Gly Cys Thr Cys Gly Ala Gly Thr Cys Thr Thr Ala Cys Thr
1               5                   10                  15

Ala Gly Thr Cys Ala Thr Thr Ala Thr Thr Ala Ala Ala Cys Thr Gly
                20                  25                  30

Cys Ala Cys Thr Thr Cys
        35

<210> SEQ ID NO 15
<211> LENGTH: 9
<212> TYPE: PRT
<213> ORGANISM: Escherichia coli

<400> SEQUENCE: 15

Thr Ile Asp Phe Ser Thr Gln Gln Ser
1               5

<210> SEQ ID NO 16
<211> LENGTH: 9
<212> TYPE: PRT
<213> ORGANISM: Escherichia coli

<400> SEQUENCE: 16

Thr Ile Lys Ser Ser Thr Cys Glu Ser
1               5
```

```
<210> SEQ ID NO 17
<211> LENGTH: 4
<212> TYPE: PRT
<213> ORGANISM: Escherichia coli

<400> SEQUENCE: 17

Ile Asp Phe Ser
1

<210> SEQ ID NO 18
<211> LENGTH: 4
<212> TYPE: PRT
<213> ORGANISM: Escherichia coli

<400> SEQUENCE: 18

Ile Glu Phe Ser
1

<210> SEQ ID NO 19
<211> LENGTH: 5
<212> TYPE: PRT
<213> ORGANISM: Escherichia coli

<400> SEQUENCE: 19

Gly Ser Tyr Phe Ala
1               5

<210> SEQ ID NO 20
<211> LENGTH: 5
<212> TYPE: PRT
<213> ORGANISM: Escherichia coli

<400> SEQUENCE: 20

Gly Ser Gly Phe Ala
1               5

<210> SEQ ID NO 21
<211> LENGTH: 5
<212> TYPE: PRT
<213> ORGANISM: Escherichia coli

<400> SEQUENCE: 21

Asp Val Thr Thr Val
1               5

<210> SEQ ID NO 22
<211> LENGTH: 5
<212> TYPE: PRT
<213> ORGANISM: Escherichia coli

<400> SEQUENCE: 22

Asp Thr Phe Thr Val
1               5

<210> SEQ ID NO 23
<211> LENGTH: 10
<212> TYPE: PRT
<213> ORGANISM: Escherichia coli

<400> SEQUENCE: 23

Val Thr Thr Val Ser Met Thr Thr Asp Ser
1               5                   10
```

<210> SEQ ID NO 24
<211> LENGTH: 10
<212> TYPE: PRT
<213> ORGANISM: Escherichia coli

<400> SEQUENCE: 24

Val Thr Ile Lys Ser Ser Thr Cys Glu Ser
1               5                   10

<210> SEQ ID NO 25
<211> LENGTH: 4
<212> TYPE: PRT
<213> ORGANISM: Escherichia coli

<400> SEQUENCE: 25

Met Glu Phe Ser
1

<210> SEQ ID NO 26
<211> LENGTH: 4
<212> TYPE: PRT
<213> ORGANISM: Escherichia coli

<400> SEQUENCE: 26

Ile Glu Phe Ser
1

<210> SEQ ID NO 27
<211> LENGTH: 9
<212> TYPE: PRT
<213> ORGANISM: Escherichia coli

<400> SEQUENCE: 27

Ala Val Leu Arg Phe Val Thr Val Thr
1               5

<210> SEQ ID NO 28
<211> LENGTH: 9
<212> TYPE: PRT
<213> ORGANISM: Escherichia coli

<400> SEQUENCE: 28

Ala Gln Leu Thr Gly Met Thr Val Thr
1               5

<210> SEQ ID NO 29
<211> LENGTH: 13
<212> TYPE: PRT
<213> ORGANISM: Escherichia coli

<400> SEQUENCE: 29

Glu Asp Gly Val Arg Val Gly Arg Ile Ser Phe Asn Asn
1               5                   10

<210> SEQ ID NO 30
<211> LENGTH: 13
<212> TYPE: PRT
<213> ORGANISM: Escherichia coli

<400> SEQUENCE: 30

Glu Ser Gly Ser Gly Phe Ala Glu Val Gln Phe Asn Asn
1               5                   10

<210> SEQ ID NO 31
<211> LENGTH: 10

```
<212> TYPE: PRT
<213> ORGANISM: Escherichia coli

<400> SEQUENCE: 31

Gln Ile Thr Gly Asp Arg Pro Val Ile Lys
1               5                   10

<210> SEQ ID NO 32
<211> LENGTH: 10
<212> TYPE: PRT
<213> ORGANISM: Escherichia coli

<400> SEQUENCE: 32

Gln Leu Thr Gly Met Thr Val Thr Ile Lys
1               5                   10
```

HIGH AFFINITY MONOCLONAL ANTIBODIES FOR DETECTION OF SHIGA TOXIN 2 (STX2)

REFERENCE TO RELATED APPLICATIONS

This application claims priority to U.S. Provisional Patent Application Ser. No. 61/707,821, filed Sep. 28, 2012, which is incorporated herein by reference in its entirety.

FIELD OF THE INVENTION

The present invention relates to high affinity monoclonal antibodies (Mab's) against Shiga toxin produced by toxin producing *Escherichia coli* and associated methods of detecting the toxin.

BACKGROUND OF THE INVENTION

Shiga toxin-producing *Escherichia coli* (STEC) are a group of prevalent foodborne pathogens responsible for outbreaks of human gastrointestinal disease. The morbidity and mortality associated with these outbreaks have highlighted the threat these organisms pose to public health (Karch et al., Int'l J Med Microbiol, (2005) 295:405-18; Gyles, J. Anim Sci, (2007) 85:E45-62; Manning et al., Emerg Infect Dis, (2007) 13:318-21). Most STEC outbreaks have been traced worldwide to the consumption of bacterial-contaminated food. Ruminants are the main reservoir for STEC strains and food contaminated with bovine feces has been linked to severe complications, such as hemorrhagic colitis (HC) and hemolytic uremic syndrome (HUS) (Hussein, J Anim Sci, (2007) 85: E63-72).

STEC possess a number of virulence factors, but Shiga toxins (Stxs) were considered the most critical in disease pathogenesis and are responsible for HC and HUS. Stxs are $AB_5$ holotoxins and are comprised of one A subunit (32 kDa) and five B subunits (7.7 kDa) (Fraser et al., Nat Struct Biol, (1994) 1:59-64; Fraser et al., J Biol Chem (2004) 279:27511-17). The Stx A subunit is an enzymatically active N-glycosidase that inhibits the activity of rRNA by cleavage of an adenine base from the 28S rRNA component of the eukaryotic ribosomal 60S subunit, causing protein synthesis to cease resulting in cell death (Endo and Tsurugi, J Biol Chem, (1988) 263:8735-9). The Stx B subunit is responsible for binding to host cells through interaction with globotriaosylceramide (Gb3) or globotetraosylceramide (Gb4) receptors present on the surfaces of cells (Lingwood, Adv Lipid Res (1993) 25:189-211), leading to subsequent internalization of the toxin. There are two serologically distinct groups of Stxs, Stx1 and Stx2. Recent epidemiological and molecular typing studies suggested that STEC strains expressing Stx2 were more virulent than strains expressing either Stx1 or both Stx1 and Stx2 (Ostroff et al., J Infect Dis, (1989) 160:994-8; Boerlin et al., J Clin Microbiol. (1999) 37:497-503). A mean lethal dose ($LD_{50}$) for Stx2 of 50 ng/kg in mice was reported by Tesh et al. (Infect Immun, (1993) 61:3392-402) and Lindgren et al. (Infect Immun, (2003) 69:623-31). In contrast to Stx1, many variants of Stx2 have been identified (Weinstein et al., J Bacteriol, (1988) 170:4223-30; Piérard et al., J Clin Microbiol (1998) 36:3317-22; Bertin et al., J Clin Microbiol, (2001) 39:3060-5; Leung et al., Appl Environ Microbiol, (2003) 69:7549-53; Strauch et al., Infect Immun, (1994) 40:338-43). These variants differ from each other in terms of their affinity for host receptors, cytotoxicity, and pathogenicity.

The capacity to control STEC disease in humans and to limit the scale of outbreaks is dependent upon prompt diagnosis and identification of the source of infection. Although the role of Stx2 in these outbreaks has received considerable attention, rapid, sensitive and specific detection methods for this toxin in food are still limited. This is because detection of Stxs in food samples is often difficult due to the combination of low toxin concentration and effect of the complex matrix present in food. Historically, the Vero cell cytotoxicity assay has played an important role in establishing a diagnosis of STEC infection and it still remains the "gold standard" for Stx activity. However, like most activity-based assays, such as the mouse bioassays, radioactivity assays, and cell-free translation assays, the Vero cell assay is time-consuming, requires cell culture facilities, and expensive equipment that is usually not available in many laboratories. Furthermore, a subsequent antibody-based neutralization bioassay is required in order to confirm the presence of the toxin. Other assays, such as receptor-based assays are less time-consuming and enable the discrimination of different toxins, but detailed evaluation and optimization are needed to establish these methods as analytical tools (Uzawa et al., ChemBioChem, (2007) 61:3392-402).

Over the past decades, a number of immunoassays have been developed, the most common ones being the enzyme-linked immunosorbent assays (ELISA). These assays provide multiple benefits. Notably, they are simple, rapid, cost-effective, and all reagents and equipment needed are available in most laboratories. However, the sensitivity and specificity of immunoassays is largely dependent on the quality of the antibodies used. Our recent studies on detecting botulinum neurotoxin type A in milk demonstrated that simple immunoassay formats can be highly sensitive when high-affinity antibodies are incorporated (Stanker et al., J Immunol Methods, (2008) 336:1-8). While antibodies against Stx2 have been described in the scientific literature, few are commercially available. Their expense and lack of sufficient binding affinity to the native toxins make studies focused on constructing a sensitive immunoassay difficult.

SUMMARY OF THE INVENTION

Herein is described the production and characterization of a collection of high affinity monoclonal antibodies (mAbs) specific to Shiga toxin (Stx2) and variants thereof. Additionally, shiga toxin specific hyridomas Stx2f-1, Stx2f-2, Stx2f-3, and Stx2f-4 and associated IgG monoclonal antibodies, specific for the shiga toxin 2f variant are disclosed herein.

An embodiment of the invention is the use of the aforementioned mAbs for use as rapid diagnostic tests for the presence of Stxs in patient, environmental and food samples.

Another embodiment is the use of the sandwich ELISA to detect Stx2 from a sample with minimal sample preparation or modification.

A further embodiment of the invention is the use of the monoclonal antibodies for in vivo treatment of exposure or infection to Stx2 (and variants thereof) or to serve as a vaccine or therapeutic agent wherein protection may be afforded via administration of the antibodies to those at risk of exposure or wherein infection or presence of the toxin within the organism has been detected.

BRIEF DESCRIPTION OF THE DRAWINGS

FIG. 1 is a photo and plot analysis of genetic toxoid of Stx2a. (A). photograph of Coomassie staining and Western blot of purified Stx2a toxoid following SDS-PAGE. Lane 1, Coomassie stained SDS-PAGE with 1 µg of purified Stx2a toxoid. Lane 2, western blot of 0.5 µg of Stx2a toxoid analyzed with mixture of mAbs against Stx2 A- and B-subunits. The A and B subunit positions are indicated by arrows at the right side and their molecular weights are labeled as kilodaltons (kDa) at the left side of the panel. (B). Effect of genetic toxoid, Stx2E167Q, on growth of vero cells. The relative cell viability was calculated by normalizing their values to the viability of cells without adding toxin as 100%. The results represent the mean±SD of three replicates from one representative experiment. Three individual experiments were performed.

FIG. 2 is a photograph of Western blots of mAb binding to Stx2a protein. FIG. 2A. Western blot of Stx2a following SDS-PAGE. Stx2a holotoxin (0.5 µg) was separated by SDS-PAGE. Membranes were probed with mAbs: 1. Stx2-1; 2. Stx2-2; 3. Stx2-3; 4. Stx2-4; 5. Stx2-5, respectively. The sizes of the Stx2a A- and B-subunits are indicated as kilodalton (kDa) at the left side of the panel. FIG. 2B. Western blot of Stx2a following native PAGE. Stx2a holotoxin (0.5 µg) was separated by native polyacrylamide gel electrophoresis. Membranes were probed with mAbs: 1. Stx2-1; 2. Stx2-2; 3. Stx2-3; 4. Stx2-4; 5. Stx2-5, respectively. The size of the Stx2a holotoxin is indicated as kilodalton (kDa) at the left side of the panel.

FIG. 3 is a graph of the binding specificity of mAbs to different variants of Stx2 by direct ELISA. Microtiter wells were coated with 1 µg/mL of the Stx2 variants, Stx2a, Stx2c, Stx2d, Stx2g, and Stx1, respectively. The binding of mAbs, Stx2-1, Stx2-2, Stx2-3, Stx2-4, and Stx2-5 to these variants were measured. The data shown represent the mean±SD of three replicates from one representative experiment. Three individual experiments were performed.

FIG. 11 is a graph of the clearance of Stx2 by monoclonal antibodies. A combination of mAbs, Stx2-1, Stx2-2, and Stx2-5 was added 2 min after toxin injection. Sera were obtained at 2, 5, 10, 20, 30 min and 1, and 2 h. MAbs accelerate Stx2 clearance, eliminating toxin from the bloodstream within minutes. The mean values for each time point were plotted along with the standard error of the mean (SEM) with n≥5.

STATEMENT OF DEPOSIT

Figure 4:
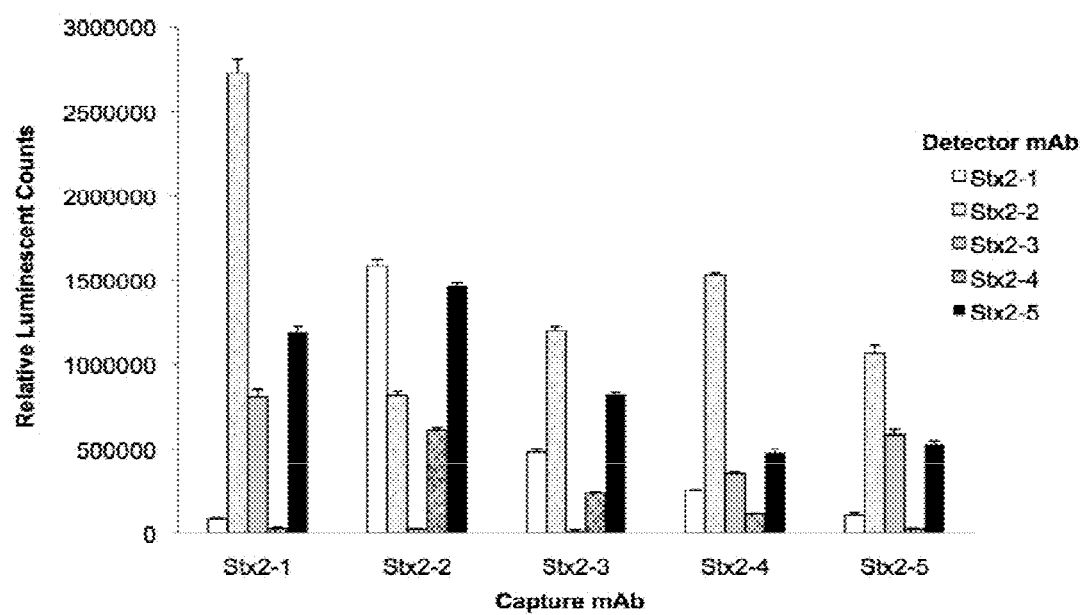
FIG. 4 is a graph of the Sandwich ELISA for detection of Stx2a. Each of the five mAbs was used as capture antibody or as the biotinylated detector antibody. Relative luminescent counts were measured for each antibody combination using Stx2a at 10 ng/mL.

Monoclonal antibodies (Mab) to Shiga toxin-producing *Escherichia coli* were deposited Mar. 12, 2013 under terms of the Budapest Treaty with the American Tissue Culture Collection (ATCC) P.O. Box 1549, Manassas, Va., 20108, USA. The Mab Stx2-1 is produced by the hybridoma deposited under American Type Culture Collection (ATCC) Accession No. PTA-13614 and recognizes Shiga toxin type 2, A subunit. Mab Stx2-2 is produced by the hybridoma deposited under American Type Culture Collection (ATCC) Accession No. PTA-13615 and recognizes Shiga toxin type 2, A and B subunits. The microorganism deposit was made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application. For the purposes of this invention, any Mab having the identifying characteristics of PTA-13614 and PTA-13615 including subcultures and variants thereof which have the identifying characteristics and activity as described herein are included.

DESCRIPTION OF THE INVENTION

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

The term "antibody" (Ab) or "monoclonal antibody" (Mab) as used herein is meant to include intact molecules as well as fragments thereof (such as, for example, Fab and F(ab') sub.2 fragments) which are capable of binding. The language "monoclonal antibody" is art-recognized terminology. The monoclonal antibodies of the present invention can be prepared using classical cloning and cell fusion techniques. The immunogen (antigen) of interest, e.g. intact shiga toxin, or a non-toxic shiga toxin derived using DNA recombinant methods, (a recombinant toxoid), or separated A or B chains of Shiga toxin, is typically administered (e.g. intraperitoneal injection to wild-type mice or transgenic mice which produce desired antibodies, such as human antibodies, rats, rabbits or other animal species which can produce native or human antibodies. The immunogen can be administered alone or as a fusion protein to induce an immune response. Fusion proteins comprise the peptide against which an immune response is desired coupled to a carrier protein, such as beta.-galactosidase, glutathione S-transferase, keyhole limpet hemocyanin (KLH), and bovine serum albumin, to name a few. In these cases, the peptides serve as haptens with the carrier proteins. After the animal is boosted, for example, three or four times, the spleen is removed and splenocytes are extracted and fused with myeloma cells using the well-known processes of Kohler and Milstein (Nature 256: 495-497 (1975)) and Harlow and Lane (Antibodies: A Laboratory Manual (Cold Spring Harbor Laboratory, New York 1988)). The resulting hybrid cells are then cloned in the conventional manner, e.g. using limiting dilution, screened and the resulting positive clones, which produce the desired monoclonal antibodies, cultured.

The term "treatment" as used herein describes neutralization of the cytotoxicity of Shiga toxin type 2 (Stx2) in vivo by administration of monoclonal antibodies as described herein, as well as, conferring protection against subsequent Stx2 toxicity when mAb is given prior to exposure.

The term "protection" as used herein describes a mammalian subject administered with a single antibody dose after exposure to Shiga toxin type 2, 3 times ip mouse LD50 or 870 ng/kg, exhibiting no signs of intoxication for a minimum of 4 weeks. One of skill in the art would understand that protection beyond the minimum time is achieved though an increase in dosage.

Human infection by Shiga toxin producing *Escherichia coli* (STEC) is one of the most prevalent foodborne diseases. Shiga toxin type 2 (Stx2) is the major contributor to hemolytic-uremic syndrome (HUS) and other systemic complications caused by STEC. Although outbreaks of HUS due to the consumption of dairy products occur frequently, very few reports are available on methods for the detection of Stx2 in milk. Herein is described the development of five high-affinity monoclonal antibodies (dissociation constants below nM range) against Stx2 using a genetic toxoid (genetically altered toxin that is no longer toxigenic) as an immunogen. These antibodies, designated Stx2-1, Stx2-2, Stx2-3, Stx2-4, and Stx2-5 are IgG1 or IgG2a heavy-chain subclass with kappa light-chains, do not cross-react with Stx1 and have different specificities to variants of Stx2. Western blot analyses following SDS-PAGE demonstrate that mAbs Stx2-2 and Stx2-5 bind both the A- and B-subunits, while the other 3 mAbs bind the A-subunit of Stx2 only. All antibodies bind stronger to the native than to the denatured Stx2 except the mAb Stx2-3, which binds equally well to both forms of the toxin. Of the five mAbs, Stx2-5 was capable of neutralizing Stx2a mediated cytotoxicity in Vero cells. A highly sensitive sandwich ELISA, capable of detecting less than 10 pg/mL of Stx2a in milk, was developed using mAb pair Stx2-1 and Stx2-2. Such an assay is useful for early recognition of STEC contamination in food and prompt implementation of control measures to prevent outbreaks. Latteral-flow devices represent an established immunoassay format. Using the Stx monoclonal antibodies in this format detection of toxin in as little as a few (0.1-5) nanograms of toxin per gram of food was achieved.

An embodiment of the invention is the use of mAbs to Stx2 for in vivo neutralization of the cytotoxicity mediated by the Stx2.

Besides supportive care, there currently are no therapeutics available for hemorrhagic colitis and hemolytic uremic syndrome induced by Shiga toxin 2 (Stx2)-producing *E. coli*. The use of antibiotics for combating pathogenic *E. coli* is not recommended because they have been shown to stimulate toxin production. Recently, Stx was observed in the circulation of children with STEC-HUS. Stx was found bound to leukocytes for up to 1 week after the diagnosis of STEC-induced diarrhea (37), which indicates the pivotal role of the toxin in the pathogenesis of disease, justifying the use of mAbs against Stx to prevent HUS in patients infected with STEC. Similar to other toxin-induced diseases (23), little endogenous serum antibody is induced against Stxs following STEC infection (3). Thus, clearing Stx2 from the circulation serves as as a modality to lessen disease severity. Herein is described the in vivo neutralization of Stx2 in mice using monoclonal antibodies (mAbs), specifically Stx2-1, Stx2-2, Stx2-4, Stx2-5, and Stx2-6. The establishment of neutralization effects proceeded via use of the ELISA described previously herein for the sensitive detection of Stx2 in mouse sera; investigation of the half-lives of Stx2 in mice, the efficacy of pre- and post-treatment of Stx2 intoxication with neutralizing antibodies and finally, monitoring the clearance of Stx2 from the circulation system by mAbs. Neutralizing mAbs were capable of clearing Stx2 completely from intoxicated mice blood within minutes. The distribution phase or t1/2 α to be 3 min and the clearance phase or t1/2 β to be 40 min based on the measured biologic half life of Stx2. The persistence of these mAbs over time and showed that complete protection could be passively conferred to mice at least 4 weeks before exposure to Stx2. An additional embodiment is the development of a simple sandwich ELISA for sensitive Stx2a detection in milk.

The Stx mAbs can be used for rapid diagnostic tests for the presence of Stxs in patient, environmental and food samples. For this purpose, a genetic toxoid of Stx2a was generated by changing a single amino acid previously shown to be critical to the enzymatic activity of the A subunit (Hovde et al., Proc Natl Acad Sci USA, (1988) 85:2568-72). Using this genetic toxoid as an immunogen is advantageous since conventional inactivation of toxin by hazardous chemicals like formaldehyde or gluteraldehyde, may result in residual toxicity (Metz et al., Vaccine, (2003) 22:156-67). Additionally, genetic toxoid preserves the holotoxin structure lost following toxoid production by formaldehyde or gluteraldehyde treatment. Thus resulting antibodies should have better binding to the native biologically active toxin; while toxoid generated by chemical or physical means is often distorted in structure and therefore, antibodies produced often react with toxoid but not the biologically active toxin (Stanker et al., J Immunol Methods, (2008) 336:1-8).

Figures 1A, 1B:
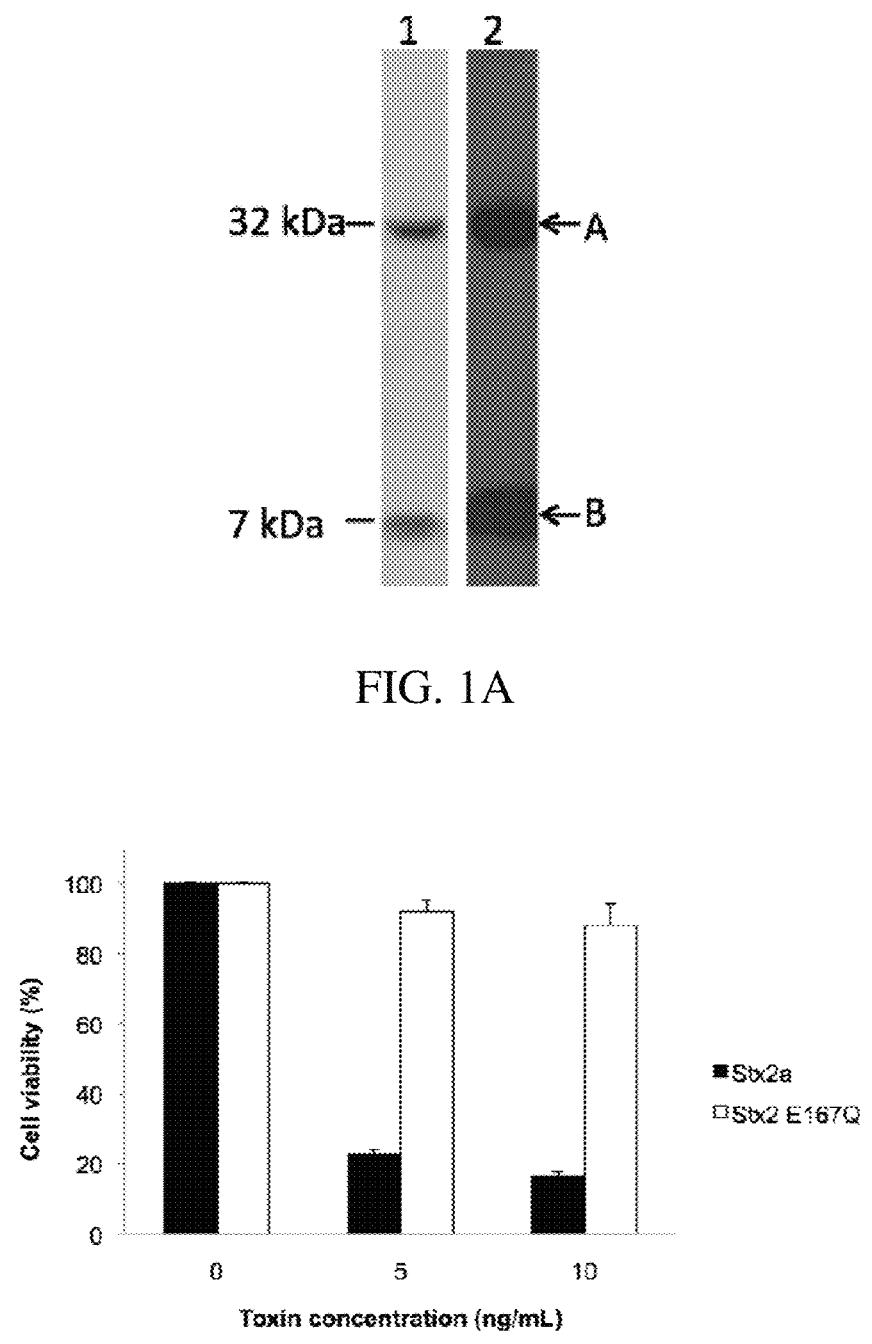

Antibodies screened with the genetic toxoid also bound the wild type, active toxin as shown by results from the ELISA (FIG. 3 and FIG. 4) and the bindings of these antibodies (except the Stx2-3) were stronger to the native Stx2a than to the denatured toxin (FIG. 2) based on the density of the protein bands on the western blots. Of the host of mAbs characterized, most were specific to the Stx2a A-subunit, only two of the mAbs bound to the B-subunit even though the amount of Stx2a B-subunit present in the toxoid preparations was similar to the A-subunit (FIG. 1)—consistent with previously reported studies (Padhye et al., J Med Microbiol, (1989) 30:219-26; Wen et al., Vaccine, (2006) 24:1142-8) suggesting that the Stx2 B-subunit is less immunogenic than the A-subunit in mice. The two mAbs, Stx2-2 and Stx2-5 bound to both the A- and B-subunits (FIG. 2a). These antibodies may recognize an epitope that spans both subunits, or they recognize a common epitope present in both subunits. Alignment of the amino acid sequences of Stx2a A and B subunits using PRSS3 (www.ch.embnet.org/software PRSS_form.html) did reveal a number of consensus sequences (Table 4.) present in both the A and B subunits. In spite of their similarities shown on the Western blot, it is clear from the toxin subtype binding experiments (FIG. 3) that the five mAbs bind different epitopes. The antibody specific for Stx2f clearly binds an epitope unique to this toxin subtype. Each mAb exhibited a unique reaction profile to four toxin variants. Exclusively binding to a single variant of Stx2 was not observed for any of the mAbs and most, except Stx2-2 bound all tested variants to some extent. Antibody cross-reactivity is not surprising because of the high similarity (>95%) in amino acid sequence among these variants (He et al., Toxins (Basel), (2012) 4:487-504).

Stx2-1 Light Chain - SEQ ID NO:1

```
                                              Framework Region 1
GAGCTCGACATTGTGCTGACCCAGACTCCCAAATTCCTGCTTGTATCAGCAGGAG
  E   L   D   I   V   L   T   Q   T   P   K   F   L   L   V   S   A   G
                                                       CDR-1
ACAGGGTTACCATAACCTGCAAGGCCAGTCAGAGTGTGAGTAATGTTGTAGCCTGGT
  D   R   V   T   I   T   C   K   A   S   Q   S   V   S   N   V   V   A   W
             Framework Region 2                         CDR-2
ACCAACAGAAGCCAGGGCAGTCTCCTAAACTGCTGATATACTATGCATCCAATCGCT
  Y   Q   Q   K   P   G   Q   S   P   K   L   L   I   Y   Y   A   S   N   R
                         Framework Region 3
ACACTGGAGTCCCTGATCGCTTCACTGGCAGTGGATATGGGACGGATTTCACTTTCA
  Y   T   G   V   P   D   R   F   T   G   S   G   Y   G   T   D   F   T   F
                                                               CDR-3
CCATCAGCACTGTGCAGGCTGAAGACCTGGCAGTTTATTTCTGTCAGCAGGAGTATA
  T   I   S   T   V   Q   A   E   D   L   A   V   Y   F   C   Q   Q   E   Y
                                 Framework Region 4
GCTCTACGTGGACGTTCGGTGGAGGCACCAAGCTGGAAATCAAACGGGCTGATGCT
  S   S   T   W   T   F   G   G   G   T   K   L   E   I   K
```

Stx2-2 Light Chain - SEQ ID NO:2

```
                                              Framework Region 1
GAGCTCGACATTGTGATGACCCAGTCTCCATCCTCCTTAACTGCCTCTCTGGGAGAA
  E   L   D   I   V   L   T   Q   S   P   S   S   L   T   A   S   L   G   E
                                                       CDR-1
GGAGTCAGTCTCACTTGTCGGACAAGTCAGGAAATTAGTGGTTACCTAAGCTGGCTT
  G   V   S   L   T   C   R   T   S   Q   E   I   S   G   Y   L   S   W   L
             Framework Region 2                         CDR-2
CAGCAGAAACCAGATGGAACTATTAAACGCCTGATCTACGCCGCATCCACTTAGAT
  Q   Q   K   P   D   G   T   I   K   R   L   I   Y   A   A   S   T   L   D
                         Framework Region 3
TCTGGTGTCCCAAAAAGGTTCAGTGGCAGTAGGTCTGGGTCAGATTATTCTCTCACC
  S   G   V   P   K   R   F   S   G   S   R   S   G   S   D   Y   S   L   T
                                                               CDR-3
ATCAGCAGCCTTGAGTCTGAAGATTTTGCAGACTATTACTGTCTACAATATGCTAGT
  I   S   S   L   E   S   E   D   F   A   D   Y   Y   C   L   Q   Y   A   S
                                 Framework Region 4
TATCCTCCGACGTTCGGTGGAGGCACCAAGCTGGAAATCAAACGGGCTGATGCT
  Y   P   P   T   F   G   G   G   T   K   L   E   I   K
```

Stx2-5 Light Chain SEQ ID NO:3

Framework Region 1
GAGCTCGATATTGTGCTGACACAGACTCCAGCCATCTTGTCTGTGAGTCCAGGAGAA
E  L  D  I  V  L  T  Q  T  P  A  I  L  S  V  S  P  G  E
                                            CDR-1
AGCGTCAGTTTCTCCTGCAGGGCCAGTCAGAACATTGGCACAGACATACAGTGGTAT
S  V  S  F  S  C  R  A  S  Q  N  I  G  T  D  I  Q  W  Y
      Framework Region 2                              CDR-2
CAGCAAAGAACAAATGGTTCTCCAAGGCTTCTCATAAAGTATGCTTCTGAGTCTATC
Q  Q  R  T  N  G  S  P  R  L  L  I  K  Y  A  S  E  S  I
                  Framework Region 3
TCTGGGATCCCTTCCAGGTTTAGTGGCAGTGGATCAGGGACAGATTTTACTCTTAGT
S  G  I  P  S  R  F  S  G  S  G  S  G  T  D  F  T  L  S
                                                      CDR-3
ATCAACAGTGTGGAATCTGAAGATGTTGCAGATTATTACTGTCAACAAAGTTATAGC
I  N  S  V  E  S  E  D  V  A  D  Y  Y  C  Q  Q  S  Y  S
                  Framework Region 4
TGGCCAACCACGTTCGGTGGAGGCACCAAGCTGGAAATCAGACGGGCTGATGCT
W  P  T  T  F  G  G  G  T  K  L  E  I  R Stx2-3 Light Chain SEQ ID NO:4

Framework Region 1
GAGCTCGATATTGTGATGACCCAAACTCCAGCAATCATGTCTGCATCTCCAGGGGAG
E  L  D  I  V  M  T  Q  T  P  A  I  M  S  A  S  P  G  E
                                            CDR-1
AAGGTCACCATGACCTGCAGTGCCAGCTCAAGTGTAAGTTACATGCACTGGTACCAG
K  V  T  M  T  C  S  A  S  S  S  V  S  Y  M  H  W  Y  Q
      Framework Region 2                              CDR-2
CAGAAGTCAGGCACCTCCCCCAAAAGATGGATTTATGACACATCCAAACTGGCTTCT
Q  K  S  G  T  S  P  K  R  W  I  Y  D  T  S  K  L  A  S
                  Framework Region 3
GGAGTCCCTGCTCGCTTCAGTGGCAGTGGGTCTGGGACCTCTTACTCTCTCACAATC
G  V  P  A  R  F  S  G  S  G  S  G  T  S  Y  S  L  T  I
                                                      CDR-3
AGCAGCGTGGACACTGAAGATGCTGCCACTTATTACTGCCAGCAGTGGAGTAGTAA
S  S  V  D  T  E  D  A  A  T  Y  Y  C  Q  Q  W  S  S  N
                  Framework Region 4
CCCAACGTTCGGTGGAGGCACCAAGCTGGAAATCAAACGGGCTGATGCT
   P  T  F  G  G  G  T  K  L  E  I  K Stx2-4 Light Chain - SEQ ID NO:5

Framework Region 1
GAGCTCGATATTGTGCTCACACAGACTACAGCCTCCCTATCTGTATCTGTGGGAG
E  L  D  I  V  L  T  Q  T  T  A  S  L  S  V  S  V  G
                                            CDR-1
AAACTGTCACCATCACATGTCGAGCCAGTGAGAATATTTACAGTAATTAGCATGGT
E  T  V  T  I  T  C  R  A  S  E  N  I  Y  S  N  L  A  W
      Framework Region 2                              CDR-2
ATCAGCAGAAACAGGGAAAATCTCCTCAGCTCCTGGTCTATGCTGCAACAAAGTTA
Y  Q  Q  K  Q  G  K  S  P  Q  L  L  V  Y  A  A  T  K  L
                  Framework Region 3
GCAGATGGTGTGCCATCAAGGTTCAGTGGCAGTGGATCAGGCACACAGTATTCCCTC
A  D  G  V  P  S  R  F  S  G  S  G  S  G  T  Q  Y  S  L
                                                      CDR-3
AAGATCAACAGCCTGCAGTCTGAAGATTTTGGGAGTTATTACTGTCAACATTTTTGG
K  I  N  S  L  Q  S  E  D  F  G  S  Y  Y  C  Q  H  F  W
                  Framework Region 4
GTTACTCCTCCGACGTTCGGTGGAGGCACCAAGCTGGAAATCAAACGGGCTGATGCT
V  T  P  P  T  F  G  G  G  T  K  L  E  I  K Stx2-1 Heavy Chain - SEQ ID NO:6

Framework Region 1
GAATTCGAAGTGAAGCTGGAGCAGTCAGGACCTGAGCTGGTGAAACCTGGGGCCTC

E F E V K L E E S G P E L V K P G A S

CDR-1

AGTGAAGATATCCTGCAAGGCTTCTGGATACACATTCATTGACTACAACATGCACTG

V K I S C K A S G Y T F I D Y N M H W

Framework Region 2

GGTGAAGCAGAGCCATGGAAAGAGCCTTGAGTGGATTGGATATATTTATCCTTACA

V K Q S H G K S L E W I G Y I Y P Y

CDR-2

ATGGTGGTACTGGCTATAATCAGAAGTTCAAGAGCAAGGCCACATTGACTGTAGAC

N G G T G Y N Q K F K S K A T L T V D

Framework Region 3

AATTCCTCCAGCACAGCCTACATGGAGCTCCGCAGCCTGACATCTGAGGACTCTGCA

N S S S T A Y M E L R S L T S E D S A

CDR-3

GTCTATTACTGTGCAAGAGTCTATAGGTACGCCTGGTTTGCTTACTGGGGCCAAGGG

V Y Y C A R V Y R Y A W F A Y W G Q G

Framework Region 4

ACTCTGGTCACTGTCTCTGCAGCCAAAACGACACCCCCATCTGTCTATAGATCTTCC

T L V T V S A A K T T P P S V Y R S S

Stx2-2 Heavy Chain - SEQ ID NO:7

Framework Region 1

GAATTCGAGGTCAAGCTGGAGGAGTCTGGACCTGGCCTGGTGGCGCCCTCACAGAG

E F E V K L E E S G P G L V A P S Q S

CDR-1

CCTTTCCATCACATGCACCGTCTCAGGGTTCTCATTAAGCGGCAATAGTGTAAACTGGGTTC

L S I T C T V S G F S L S G N S V N W V

Framework Region 2

GCCAGCCACCAGGAAAGGGTCTGGAGTGGCTGGGCATGATATGGGGTGATGGAACCACAGA

R Q P P G K G L E W L G M I W G D G T T D

CDR-2

CTATAATTCAACTCTCAAATCCAGACTGAGCATCTGGAAGGACAATTCCAAGAGCCAAGTTC

Y N S T L K S R L S I W K D N S K S Q V

Framework Region 3

TCTTAAAAATGAACAGTCTGCAAACTGATGACACAGCCAGATACTACTGTGCCTTCCGACAT

L L K M N S L Q T D D T A R Y Y C A F R H

CDR-3 Framework Region 4

TACTACGGCATCGGCTATGCTATGGACTACTGGGGKYAAGGAACCTCACTCACCGTCTCCTCA

Y Y G I G Y A M D Y W G X G T S L T V S S

Stx2-5 Heavy Chain - SEQ ID NO:8

Framework Region 1

GAATTCGAGGTCAAGCTGGAGCAGTCTGGAGGAGACTTAGTGAAGCCTGGAGGGTC

E F E V K L E Q S G G D L V K P G G S

CDR-1

CCTGAAACTCTCCTGTGCAGCCTCTGGATTCACTTTCAGTACTTATGGCATGTCTTGG

L K L S C A A S G F T F S T Y G M S W

Framework Region 2

GTTCGCCAGACTCCAGACAAGAAACTGGAGTGGGTCGCAACCATTAGTTATGGTTAT

V R Q T P D K K L E W V A T I S Y G Y

CDR-2

ACTTACACCTACTATCCAGACAGTGTGAAGGGGCGATTCACCATTTCCAGAGACAAT

T Y T Y Y P D S V K G R F T I S R D N

Framework Region 3

GCCCAGAACACCCTGTACCTACAAATGAGCAGTCTGAACTCTGAGGACACAGCCAT

A Q N T L Y L Q M S S L N S E D T A M

CDR-3

GTATTACTGTGTAAGACGGGAAGATCACGGGGCTATGGACTACTGGGGTCAAGGAA

Y Y C V R R E D H G A M D Y W G Q G

Framework Region 4

CCTCAGTCACCGTCTCCTCAGCCAAAACGACACCCCCATC

T S V T V S S A K T T P P S

Stx2-3 Heavy Chain - SEQ ID NO:9

Framework Region 1
GAATTCGAAGTGAAGCTGGAGGAGTCAGGGGCTGAACTGGCAAGACCTGGGGCCTC
 E  F  E  V  K  L  E  E  S  G  A  E  L  A  R  P  G  A  S
                                                       CDR-1
AGTGAAGATGTCCTGCAAGGCTTCTGGCTACATCACGATGCACTGGATAAAACAGA
 V  K  M  S  C  K  A  S  G  Y  I  T  M  H  W  I  K  Q
    Framework Region 2                              CDR-2
GGCCTGGACAGGGTCTGGAATGGATTGGATACATTAATCCTAACAGTGGTTATACTA
 R  P  G  Q  G  L  E  W  I  G  Y  I  N  P  N  S  G  Y  T ATTACAATCAGAAGTTCAAGGACAAGGCCACAATGACTGCGGACAAATCCTCTAGT
 N  Y  N  Q  K  F  K  D  K  A  T  M  T  A  D  K  S  S  S
              Framework Region 3
ACAGTCTACATGCAACTGAACAGCCTGACATCTGATGACTCTGCAGTCTATTACTGT
 T  V  Y  M  Q  L  N  S  L  T  S  D  D  S  A  V  Y  Y  C
                        CDR-3
GCAAGAGAGGGTTTATTACGGCCCGATTACCATGCTCTGGACTACTGGGGTCAAGG
 A  R  E  G  L  L  R  P  D  Y  H  A  L  D  Y  W  G  Q  G
    Framework Region 4
AACCTCAGTCACCGTCTCCTCAGCCAAAACGACACCCCCATCTGTCTATAGATCTTCC
 T  S  V  T  V  S  S  A  K  T  T  P  P  S  V  Y  R  S  S Stx2-4 Heavy Chain - SEQ ID NO:10

Framework Region 1
GAATTCCAGGTGAAGCTGCAGGAGTCTGGACCTGAGCTGAAGAAGCCTGGAGAGAC
 E  F  Q  V  K  L  Q  E  S  G  P  E  L  K  K  P  G  E  T
                                                       CDR-1
AGTCAAGATCTCCTGCAAGGCTTCTGGGTATACCTTCACAAACTATGGAATGAACTG
 V  K  I  S  C  K  A  S  G  Y  T  F  T  N  Y  G  M  N  W
    Framework Region 2
GGTGAAGCAGGCTCCAGGAAAGGGTTTAAAGTGGATGGGCTGGATTACCACCTACA
 V  K  Q  A  P  G  K  G  L  K  W  M  G  W  I  T  T  Y
    CDR-2
CTGGAGAGCCAACATATGCTGATGACTTCAAGGGACGGTTTGCCTTCTCTTTGGAAA
 T  G  E  P  T  Y  A  D  D  F  K  G  R  F  A  F  S  L  E
              Framework Region 3
CCTCTGCCAGCACTGCCTATTTGCAGATCAACAACCTCAAAAATGAGGACTCGGCTA
 T  S  A  S  T  A  Y  L  Q  I  N  N  L  K  N  E  D  S  A
                        CDR-3
CATATTTCTGTGTTAGATATGGTAACTTCAGAGGATACTTCGATGTCTGGGGCGCAG
 T  Y  F  C  V  R  Y  G  N  F  R  G  Y  F  D  V  W  G  A
    Framework Region 4
GGACCACGGTCACCGTCTCCTCAGCCAAAACGACACCCCCATCTGTCTATAGATCT
 G  T  T  V  T  V  S  S  A  K  T  T  P  P  S  V  Y  R  S

TABLE 1

| Oligonucleotide sets for mutagenesis in stx2A | |
|---|---|
| Primers | Sequence* |
| Primers for PCR fragment 1 | |
| Stx2A-F2 (Nde I) | 5'-GGAATTCCATATGAAGTGTATATTATTTAAATG-3' SEQ ID NO: 11 |
| Stx2 E167Q-R | 5'-CGTAAGGCTTGTGCTGTGAC-3' SEQ ID NO: 12 |
| Primers for PCR fragment 2 | |
| Stx2 E167Q-F | 5'-GTCACAGCACAAGCCTTACG-3' SEQ ID NO: 13 |
| Stx2B-R1 (Xho I) | 5'-CCGCTCGAGTCTTACTAGTCATTATTAAACTGCACTTC-3' SEQ ID NO: 14 |
| Second round PCR primers | |
| Stx2A-F2 (Nde I) | As above |
| Stx2B-R1 (Xho I) | As above |

*Sites of mutagenesis are highlighted in gray.

TABLE 2

Some characteristics of the Stx2 monoclonal antibodies.

| Antibody | Isotype | Specificity | KD (×10$^{-9}$M)* |
|---|---|---|---|
| Stx2-5 | IgG1, kappa | A&B-subunit | 0.28 ± 0.08 a |
| Stx2-2 | IgG2a, kappa | A&B-subunit | 0.71 ± 0.06 b |
| Stx2-1 | IgG1, kappa | A-subunit | 1.28 ± 0.04 c |
| Stx2-4 | IgG1, kappa | A-subunit | 1.46 ± 0.01 c |
| Stx2-3 | IgG1, kappa | A-subunit | 1.55 ± 0.03 c |

*Differences between numbers with the same letter were not statistically significant and between numbers with different letters were statistically significant (P < 0.05)

TABLE 3

Percent recovery of Stx2a from milk using a sandwich immunoassay (%)

| Spike level (pg/mL) | 10 | 100 | 200 | 400 |
|---|---|---|---|---|
| 2% Milk | 125 ± 6.36 | 100 ± 2.7 | 90 ± 3.2 | 90 ± 0.5 |
| whole milk | nd* | 114 ± 5.8 | 99 ± 4.1 | 90 ± 9.7 |

*Not detectable.
Data shown is the average of three replicates ± standard deviation.

TABLE 4

Alignment of amino acid consensus sequences between A- and B-subunits of Stx2a.

| Subunit | Amino acids | Position | Consensus* | |
|---|---|---|---|---|
| A | TIDFSTQQS | 4-12 | TIxxSTxxS | SEQ ID NO: 15 |
| B | TIKSSTCES | 50-58 |  | SEQ ID NO: 16 |
| A | IDFS | 5-8 | IxFS | SEQ ID NO: 17 |
| B | IEFS | 8-11 |  | SEQ ID NO: 18 |
| A | GSYFA | 47-51 | GSxFA | SEQ ID NO: 19 |
| B | GSGFA | 59-63 |  | SEQ ID NO: 20 |
| A | DVTTV | 102-106 | DxxTV | SEQ ID NO: 21 |
| B | DTFTV | 17-21 |  | SEQ ID NO: 22 |
| A | VTTVSMTTDS | 103-112 | VTxxSxTxxS | SEQ ID NO: 23 |
| B | VTIKSSTCES | 49-58 |  | SEQ ID NO: 24 |
| A | MEFS | 143-146 | xEFS | SEQ ID NO: 25 |
| B | IEFS | 8-11 |  | SEQ ID NO: 26 |
| A | AVLRFVTVT | 157-165 | AxLxxxTVT | SEQ ID NO: 27 |
| B | AQLTGMTVT | 42-50 |  | SEQ ID NO: 28 |
| A | EDGVRVGRISFNN | 215-227 | ExGxxxxxxFNN | SEQ ID NO: 29 |
| B | ESGSGFAEVQFNN | 57-69 |  | SEQ ID NO: 30 |
| A | QITGDRPVIK | 261-270 | QxTGxxxxIK | SEQ ID NO: 31 |
| B | QLTGMTVTIK | 43-52 |  | SEQ ID NO: 32 |

*x is any amino acid.

It has been reported that Stx1 and Stx2 share about 60% deduced amino acid sequence homology (Jackson et al., Microb Patholog, (1987) 2:147-53). Reports in the literature about whether these two toxins are antigenically distinct have been contradictory (Wen et al., Vaccine, (2006) 24:1142-8; Jeong et al., J Infect Dis, (2010) 201:1081-3). Our results indicated that the five mAbs developed from the Stx2a molecularly derived toxoid-immunized mice reacted only to Stx2, but not to Stx1 (FIG. 3) in the capture ELISA used in these tests, supporting that Stx1 and Stx2 are distinct antigens for mice.

Very little is known about the quantity of Stxs produced and the conditions required for Stx production by STEC in food, in part because of the lack of sensitive methods to detect the toxin in food. As such, an embodiment of the invention is the development of a sensitive method to detect Stx2 in milk. The high affinities of the antibodies developed here allow them to be used to develop a sensitive sandwich ELISA to detect Stx2a. The most sensitive sandwich ELISA used the mAb, Stx2-1, as a capture antibody and the biotinylated mAb, Stx2-2, as a detector antibody (FIG. 4). This sandwich ELISA is capable of detecting less than 10 pg/mL of Stx2a in 2% milk, which is 50-fold more sensitive than published results (Weeratna and Doyle, Appl Environ Microbiol, (1991) 57:2951-5). The sensitivity of Stx2 detection assays in milk may be improved after removing the matrix effect by simple dilutions and also that this method could be applied to other samples with complex matrices.

Antibodies, or fragments thereof, may be labeled using any of a variety of labels and methods of labeling. Examples of types of labels which can be used in the present invention include, but are not limited to, enzyme labels, radioisotopic labels, non-radioactive isotopic labels, chromogenic labels, fluorescent labels, and chemiluminescent labels [Harlow and Lane, Antibodies: A Laboratory Manual (Cold Spring Harbor Laboratory, New York 1988) 555-612].

A further embodiment is a method for detecting Stx2 in a sample containing Stx2. The method includes contacting the sample with an antibody by binding to a capture antibody which is then detected with the detector antibody. The detector antibody can be directly labeled with enzymes, fluorphores etc and thus is directly detected. The detector antibody in the present assay is labeled with biotin. Biotin has a strong binding to avidin that is further conjugated to enzymes, labels etc. Substrate is added and color, luminescence, fluorescence is measured and is directly proportional to the amount of toxin captured. The sample can be biological, environmental or a food sample.

The language "detecting the formation of the immunological complex" is intended to include discovery of the presence or absence of Stx2 in a sample. The presence or absence of Stx2 can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988) 555-612. Such immunoassays include antibody capture assays, antigen capture assays, two-antibody sandwich assays, lateral flow immunoassays, and immunoaffinity assays. These assays are commonly used by those of ordinary skill in the art. In an antibody capture assay, the antigen is attached to a solid support, and labeled antibody is allowed to bind. After washing, the assay is quantitated by measuring the amount of antibody retained on the solid support.

A variation of this assay is a competitive ELISA—as represented by an embodiment of the invention—wherein the antigen is bound to the solid support and two solutions containing antibodies which bind the antigen, for example, serum from a Stx2 vaccinee, and a monoclonal antibody of the present invention, are allowed to compete for binding of the antigen. The amount of monoclonal bound is then measured, and a determination is made whether the serum contains anti Stx antibodies wherein detection of large amounts of monoclonal antibody indicates a small to no antibody against Stx in the serum. This competitive ELISA can be used to predict immunity in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen. These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations.

Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), Schurs, A. H. W. M., et al. 1977 (Clin. Chim Acta 81:1-40), Bobrovnik, S. A. 2003 (J. Biochem. Biochys. Methods 57:213-236), and Friguet et al 1985 (J. Immunol. Methods 77:305-319).

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, betagalactosidase, ribonuclease, urease, catalase, glucose-6-phosphate dehydrogenase, glucoamylase, acetylcholine esterase, etc.

Examples of suitable radioisotopic labels include $^3$H, $^{125}$I, $^{131}$I, $^{32}$P, $^{35}$S, $^{14}$C, $^{51}$Cr, $^{57}$Co, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, and $^{109}$Pd.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of chemiluminescent substrates include a luminal substrate, an isoluminal substrate, an aromatic acridinium ester substrate, an imidazole substrate, an acridinium salt substrate, an oxalate ester label, a luciferin substrate, a luciferase label, an aequorin label, etc.

Compositions of the present invention can be formulated according to known methods to prepare pharmaceutically useful compositions, whereby these materials, or their functional derivatives, are combined in admixture with a phamaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, metheylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid), agars, agarose, or ethylene vinylacetate copolymers. Alternatively, instead of incorporating these agents into polymeric particles, it is possible to entrap these materials in microcapsules prepared, for example, interfacial polymerization, for example, hydroxymethlcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the antibodies disclosed herein may be carried out by any suitable means known to one of skill in the art, including parenteral injection (such as intraperitoneal, subcutaneous, or intramuscular injection), orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1 or more separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 months and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

An embodiment of the invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

Materials and Methods
Construction of Stx2a Genetic Toxoid

The glutamic acid at position 167 of the A subunit is a critical residue in the active site for enzymatic activity of Stx1 and Stx2 (Hovde et al., Proc Natl Acad Sci USA, (1988) 85:2568-72; Gordon et al., Infect Immun, (1992) 60:485-90, therefore, a mutation was introduced at this position. The change of glutamate (Q) to glutamine (E) was directed by PCR using bacterial strain EDL933 (O'Brien et al., Lancet, (1983) 8326 Pt 1:702) genomic DNA and primer pairs for PCR fragments 1 and 2 (Table 1). The full-length recombinant mutant stx2a was generated by connecting 2 fragments through a second round of PCR using the primer pair, Stx2A-F2 and Stx2-R1. The DNA fragment from the second round PCR was digested with Nde I and Xho I and cloned into the pQE-T7-2 vector (Qiagen, Valencia, Calif.). The introduced mutation was confirmed by DNA sequencing using the ABI PRISM BIGDYE Terminator Sequencing Kit (Applied Biosystems, Foster City, Calif.).

Purification of Stx2a Genetic Toxoid

The plasmid containing mutant stx2a was transformed into BL21(DE3) pLysS competent cells (Promega, Madison, Wis.) and the cells were grown overnight at 30° C. in Luria-Bertani (LB) medium with 50 µg/mL kanamycin. The overnight culture was diluted at 1:50 in LB with kanamycin and continuously grown at 30° C. to OD600 0.6, then induced with IPTG (1 mM) overnight at 20° C. The bacteria were sedimented by centrifugation, then lysed in 1/10 volume of phosphate-buffered saline (PBS) by sonication. The lysate was clarified by centrifugation and concentrated by precipitation at room temperature with saturated ammonium sulfate added to a final concentration of 60%. The precipitate was pelleted by centrifugation at 10,000 g for 10 minutes and resuspended in 0.01 M PBS with 0.138 M NaCl and 0.0027 M KCl, pH7.4 (Sigma, St. Louis, Mo.). After desalting using a ZEBA Spin Desalting Column (7K MWCO, Pierce Biotechnology, Rockford, Ill.), samples containing the Stx2a toxoid were affinity purified using a column containing an immobilized monoclonal antibody (mAb) against the Stx2 A-subunit (VT135/6-B9, Sifin Institute, Berlin, Germany). The immunoaffinity column was generated using an AMINOLINK PLUS Immobilization Kit (Pierce, Biotechnology) and toxoid was purified following the manufacturer's instruction. Concentration of the toxoid was determined using a BCA Protein Assay Kit (Pierce, Rockford, Ill.) and purity of the preparation was examined by sodium dodecyl sulfate-polyacrylmide gel electrophoresis (SDS-PAGE). Loss of toxicity of the toxoid was assessed using the Vero cell cytotoxicity assay (Neal et al., Infect Immun, (2010) 78:552-61).

Source of Stx1 and Stx2 Variants

Pure Stx1 was purchased from List Biological Laboratories, Inc. (Campbell, Calif.). The Stx2 variants, Stx2a, Stx2c, Stx2d, and Stx2g were purified from culture supernatants of bacterial strains RM10638, RM10058, RM8013, and RM10468 (kindly provided by Dr. Robert E. Mandrell at USDA, ARS, WRRC) and prepared as described previously (He et al., Toxins (Basel), (2012) 4:487-504).

Monoclonal Antibody Production

Hybridoma medium (HM) consisted of Iscove's modified Dulbecco's Minimal Medium (Sigma #1-7633) containing NaHCO$_3$ (36 mM), and glutamine (2 mM). All hybridoma cells and SP2/0 mouse myeloma cells were maintained in HM supplemented with 10% fetal calf serum (cHM). Hybridomas were selected following cell fusion using HAT selection medium prepared by adding hypoxanthine (5 µM), aminopterin (0.2 µM), and thymidine (0.8 µM) to cHM. Macrophage conditioned medium (MPCM) was prepared as described (Sugasawara et al., J Immunol Methods (1985) 79:263-75). A mixture of cHM and 40% MPCM was used for all cell-cloning procedures.

Immunization and Sample Collection

Female Balb/cJ mice (Simonsen Laboratories, Gilroy, Calif.) were immunized at 2-week intervals by intraperitoneal injection (IP) of 100 µL of Stx2a toxoid (50 µg/mL) in Sigma Adjuvant System (Sigma, St. Louis, Mo.). Following the third injection, serum was obtained (50 µL/mouse) and evaluated for anti-Stx2 antibodies. After 2 weeks, mice with a strong antibody titer were boosted by IP injection with a single dose of Stx2a toxoid (100 µL at 10 µg/mL in PBS without adjuvant).

Fusion Procedure

Three days following the last IP injection mice were euthanized and their splenocytes were fused with SP2/0 myeloma cells using polyethylene glycol as previously described (Bigbee et al., Mol Immunol, (1983) 20:1353-62). Following cell fusion, the cells were suspended in 100 mL of HAT selection medium supplemented with 10% fetal calf serum and 10% MPCM, dispensed into ten 96-well tissue culture plates, and incubated for 10 to 14 days at 37° C. in 5% CO2 before screening for antibody production.

Screening Methods

Sera from immunized mice and supernatants from cell fusion plates were screened using an ELISA. BLACK MAXISORP 96-well Nunc microtiter plates (Thermo Fisher Scientific Inc., Waltham, Mass.) were coated with 100 µL/well of a 1 µg/mL of Stx2a in PBS by overnight incubation at 4° C. The toxin solution was aspirated and non-coated sites were blocked by adding 300 UL/well of 5% non-fat dry milk in 0.02 M Tris buffered saline with 0.9% NaCl, pH 7.4 and 0.05% Tween-20 (NFDM-TBST). The plates were incubated for 1 hour at 37° C. and then washed two times with TBST. Next, sera or cell culture supernatants were added (100 µL/well) and the plates were incubated at 37° C. for 1 hour. Plates were washed 6 times and 100 µL/well of a 1:5,000 dilution of HRP conjugated goat anti-mouse IgG (H+L) (GAM-IgG-HRP) (Promega, Madison, Wis.) was added and the plates were incubated for 1 hour at 37° C. The plates were then washed six times with TBST. Freshly prepared SUPERSIGNAL West Pico Chemiluminescent Substrate (Pierce, Rockford, Ill.) was added (100 µL/well) according to the manufacturer's recommendation. The plates were incubated for 3 minutes at room temperature and luminescent counts were measured using the VICTOR-3 microplate reader (Perkin-Elmer, Shelton, Conn.).

Antibody Production and Purification

Cells from the wells producing antibodies that bound to Stx2a were cloned by limiting dilution. Hybridomas were then expanded and ascites fluids (10 to 30 mL) were obtained (Covance Research Products, Inc., Denver, Pa.). Antibodies were purified by affinity chromatography on Protein-G conjugated Sepharose (Sigma, #P-32196) and bound antibodies were eluted with 0.1 M glycine-HCl, pH 2.7. Protein concentrations were determined with the BCA Protein Assay Kit (Pierce). The attachment of biotin to antibodies was performed using a LIGHTNING-LINK Biotin Conjugation Kit (Innova Biosciences, Cambridge, UK). Antibody isotype was determined by ELISA using toxin-coated microtiter plates and horseradish peroxidase-conjugated, isotype-specific antibodies (SouthernBiotech, Birmingham, Ala.).

Characterization of mAbs

In order to identify the best antibody pair for a capture ELISA all possible pairs of mAbs were evaluated. Black NUNC plates were individually coated with each mAb (100 µL/well of a 1 µg/mL solution in PBS) and incubated overnight at 4° C. Plates were then blocked by adding 300 µL of 3% bovine serum albumin (BSA) in TBST and incubating for 1 hour at 37° C. Next, plates were washed two times with TBST and stored for up to 10 days at 4° C. before use. After toxin standards and samples (100 µL/well in PBS) were added, the plates were incubated for 1 hour at 37° C. and then washed six times with TBST. Next, each mAb was biotinylated and used as the detection antibody (100 µL/well of a 1 µg/mL solution in 3% BSA-TBST). The plates were incubated for 1 hour at 37° C. The plates were washed six times with TBST and then 100 µL/well of 1:20,000 dilution of streptavidin-HRP (Invitrogen, Carlsbad, Calif.) in 3% BSA-TBST was added. The plates were incubated for 1 hour at 37° C. Finally, the plates were washed six times with TBST and SUPERSIGNAL West Pico Chemiluminescent Substrate (Pierce) was added. The Limit of Detection (LOD) was defined as the lowest toxin concentration at which the average ELISA reading was three standard deviations above the negative control.

All gel electrophoresis equipment, buffers, gels and PVDF membranes were purchased from Invitrogen. Toxin-specificity of each mAb was analyzed by western blot. Purified wild type Stx2a was separated by Native- or SDS-PAGE using 4-12% Native or NuPAGE (denatured) Novex Bis-Tris mini gels following the manufacturer's protocol. To visualize proteins directly after gel electrophoresis, 2 µg of toxin was loaded in each lane and gels were stained with Coomassie Blue G-250 (Bio-Rad, Hercules, Calif.). For western blot analysis, 0.5 µg of toxin was loaded and separated by PAGE. Proteins were electrotransferred to a PVDF membranes (0.45 um). The membranes were blocked with 5% NFDM, then probed with mouse serum (1:10,000) or anti-toxin mAbs (20 µg/mL), followed by GAM-IgG-HRP (1:500,000). Bound antibody was detected using the Amersham ECL-Plus Western Blotting Detection System (GE Healthcare, UK) according to the manufacturer's protocol.

Antibody-Antigen Binding Affinity Measurements

Real time binding assays between purified antibodies and purified Stx2a protein were performed using biolayer interferometry with an OCTET QK system (Forte-bio, Menlo Park, Calif.). The system measures light interference on the surface of a fiber optic sensor, which is directly proportional to the thickness of molecules bound to the surface. Targets of interest are chemically tethered to the surface of the sensor using biotin-streptavidin interactions. Binding of a partner molecule to the tethered target results in thickening of the surface, which is monitored in real time. In this study, the biotinylated mAbs were coupled to kinetics grade streptavidin biosensors (Forte-bio) at 10 µg/mL in PBS. Unbound antibodies were removed from the surface of the sensors by incubation in PBS. Probes coupled to antibody were allowed to bind to Stx2a at seven different concentrations ranging from 2 to 142 nM. Binding kinetics were calculated using the OCTET QK software package (Data Acquisition 7.0), which fit the observed binding curves to a 1:1 binding model to calculate the association rate constants. The Stx2a protein was allowed to dissociate by incubation of the sensors in PBS. Dissociation kinetics were calculated using the Octet QK software package, which fit the observed dissociation curves to a 1:1 model to calculate the dissociation rate constants. Equilibrium dissociation constants were calculated as the kinetic dissociation rate constant divided by the kinetic association rate constant. Statistical differences between dissociation constants were analyzed by One Way Anova, Tukey's Multiple Comparison Test using GRAPHPAD PRISM 5 (GraphPad Software Inc., San Diego, Calif.). Differences between numbers were considered significant at $P<0.05$.

Neutralization of Stx2a Mediated Cytotoxicity in Vero Cells

An in vitro cytotoxicity assay was used to evaluate the neutralization ability of the mAbs. Fresh Vero cells were seeded on 96-well plates at $1\times10^5$ cells/ml (100 µL/well) overnight in Dulbecco's Modified Eagle Medium (DMEM, Invitrogen) supplemented with 10% fetal calf serum (Invitrogen) and incubated in a humidified incubator (37° C., 5% $CO_2$). Cells were first treated with Stx2a (10 ng/mL), mAb (20 µg/mL), or Stx2a (10 ng/mL) plus mAb (20 µg/mL) at 4° C. for 1 hour, then shifted to 37° C. overnight. The cytotoxicity was assessed using CELLTITER-GLO reagent (Promega) according to the manufacturer's instruction, except that the reagent was diluted 1:5 in PBS prior to use. Luminescence was measured with a VICTOR 3 plate reader (Perkin Elmer). All treatments were performed in triplicate. Cells grown in medium without toxin were used as a negative control (0% toxicity). The cytotoxicity for cells was calculated as follows: [(cps from negative control−cps from samples treated)/cps from negative control]×100. The relative cytotoxicity after neutralization was calculated by normalizing the toxicity of Stx2 without neutralization by mAb as 100%.

Assessment of the Stx2a Toxoid

It was reported that the glutamic acid at position 167 of the A-subunit was the active site for enzyme activity for both Stx1 and Stx2 (Hovde et al., Proc Natl Acad Sci USA (1988) 85:2568-72; Jackson et al., J Bacteriol, (1990) 172:3346-50; Wen et al., Vaccine, (2006) 24:1142-8). Therefore, the glutamate at this position was changed to glutamine. The purity of the toxoid, Stx2 E167Q, prepared in this study was assessed following SDS-PAGE by Coomassie staining and western blot with a mixture of commercial mAbs, VT135/6-B9 and VT136/8-H4 against the Stx2 A- and B-subunit (Sifin Institute, Germany). Two protein bands were observed with molecular weights of approximately 32 kDa and 7 kDa, corresponding to the sizes of the A and B subunit of Stx2 and no contaminating proteins were visible in the toxoid preparation (FIG. 1a).

Next, the cytotoxicity was assessed in Vero cells to confirm that the toxoid was non-toxic. FIG. 1b shows the observed cell viability (92% and 89%) when cells were treated with this toxoid at concentrations of 5 and 10 ng/mL [500 and 1000 times the cytotoxic dose (CD50) of the native toxin, respectively].

Isolation and Characterization of Monoclonal Antibodies Against Stx2

To identify mAbs against Stx2, we screened 2000 culture wells following two splenocyte-myeloma cell fusions. Positive signals (signal-to-noise of 5 or greater) were observed for 127 of the supernatants. The cells from these wells were expanded, tested, and cloned by limiting dilution to produce hybridoma lines. Of these hybridomas, we chose 5 for further investigation based on mAb affinity, subunit specificity, and neutralization activity. These antibodies designated Stx2-1, Stx2-2, Stx2-3, Stx2-4, and Stx2-5 were further characterized. Table 2 summarized the results of the antibody characterization studies. Isotype analysis demonstrated that mAbs Stx2-1, Stx2-3, Stx2-4, and Stx2-5 have IgG1, and that mAb Stx2-2 has an IgG2a type heavy chain. All of the mAbs possess kappa light-chains. In order to determine the subunit-specificity for each antibody, pure Stx2a was probed by Western blot following SDS-PAGE (FIG. 2a). These results demonstrate that mAbs Stx2-1, Stx2-3, and Stx2-4 bound to the A-subunit. In contrast, mAbs Stx2-2 and Stx2-5 bound to both A- and B-subunits. In addition, an unknown protein band above the A-subunit was bound by these two antibodies. Western blots following native gel electrophoresis of Stx2a indicate that all five mAbs were able to bind the native holotoxin (FIG. 2b). Four of the mAbs had weaker binding on the Western blots following SDS-PAGE (denatured Stx2a) compared to binding following native gel electrophoresis. Monoclonal antibody Stx2-3 exhibited strong binding to both denatured and native Stx2a protein (compare FIGS. 2a and 2b). All five mAbs failed to bind to the Stx2a denatured by heat at 100° C. for 5 minutes when tested by direct binding ELISA.

Quantitation of mAb/Stx2 Binding Affinity

To confirm the specificity of the mAbs and to quantitate the affinity of each antibody for the Stx2a protein, we used biolayer interferometry to examine mAb binding to purified Stx2a protein. In these experiments, the antibodies were chemically coupled to biotin and conjugated to the surface of streptavidin-coated fiber optic probes. The conjugated probes were placed in solutions with different concentrations of the Stx2a protein. Binding of the Stx2a to each antibody on the surface of the probes was measured by the change in interference from light reflected from the surface of the probe. Kinetics of equilibrium dissociation constants were calculated assuming a 1:1 binding ratio using the manufacturer's software (Table 2). As expected from western blot results, all five of the antibodies bound to the Stx2a protein. Stx2-5 showed the strongest binding, with a dissociation constant of $0.38 \times 10^{-9}$ M. Next was mAb, Stx2-2, with a dissociation constant of $0.71 \times 10^{-9}$ M. The dissociation constant of mAbs Stx2-1, Stx2-3, and Stx2-4 for Stx2 were similar and lower, with dissociation constants of $0.13 \times 10^{-8}$ M, $0.14 \times 10^{-8}$ M, and $0.15 \times 10^{-8}$ M, respectively.

Specificity of mAbs in Direct Binding ELISA

Figure 3:
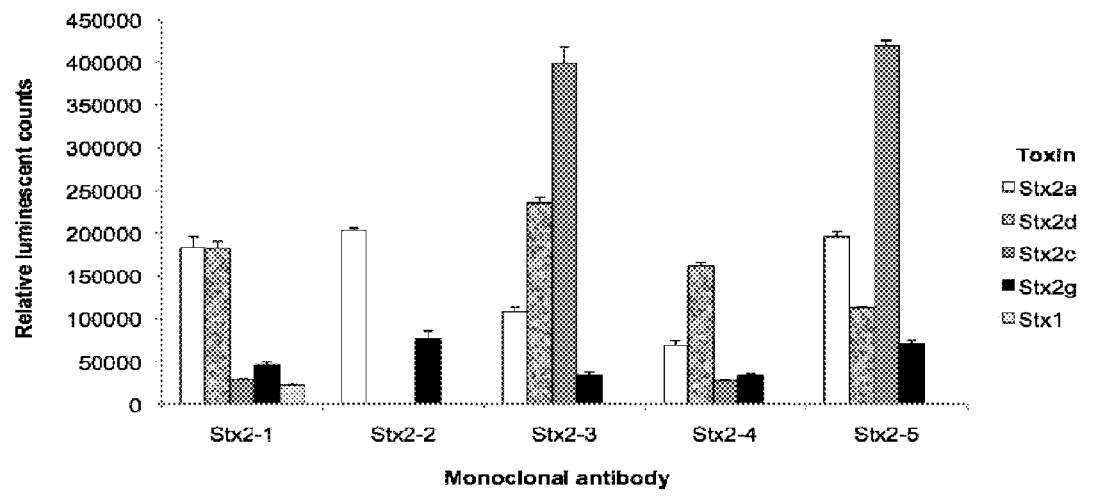

The ability of five mAbs to bind Stx1 and different variants of Stx2 was evaluated by ELISA. In these experiments Stx1 and four Stx2 variants available in the laboratory were absorbed onto microplates in PBS buffer. It appears that the five mAbs do not bind Stx1 and have different binding preferences to the four variants of Stx2 (FIG. 3). The mAb Stx2-2 bound to Stx2a and Stx2g with virtually no binding to the Stx2c and Stx2d. The mAbs Stx2-3 and Stx2-5 bound very well to Stx2c, poorly to Stx2g, and intermediately to Stx2a and Stx2d. The mAbs Stx2-1 bound equally well to Stx2a and Stx2d but poorly to the other toxin variants. The mAb Stx2-4 preferentially bound Stx2d and had lower reactivity to the toxins overall compared with other mAbs. These results indicate that the five mAbs are Stx2-specific and distinct from one another, suggesting that they recognize different epitopes.

3.5. Sandwich ELISA

Figure 5:
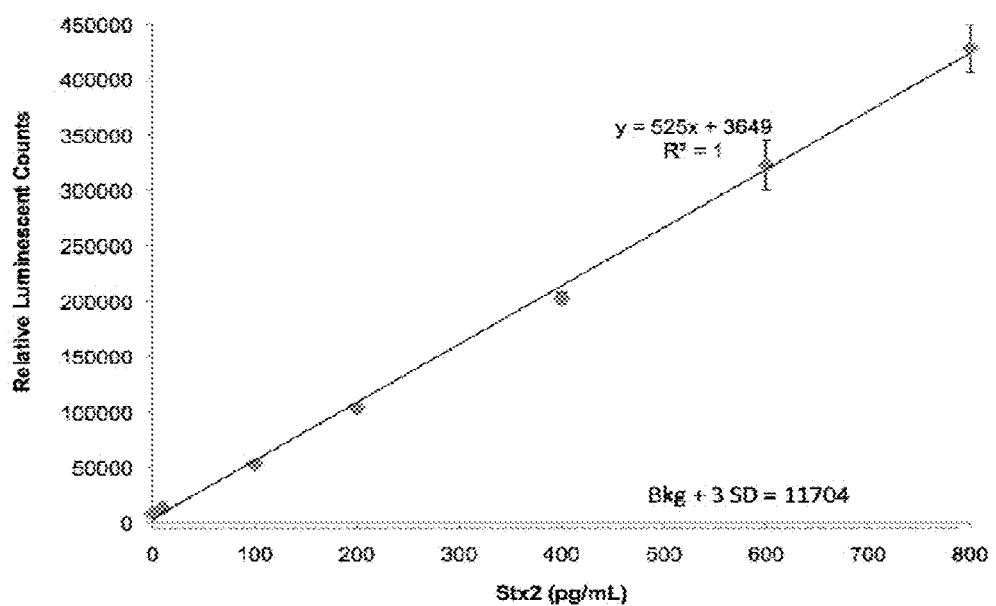
FIG. 5 is a graph of the detection of Stx2a in PBS using mAb Stx2-1 as capture antibody and Stx2-2 as detector antibody. Diamonds represent the average of three determinations±one SD. Horizontal dashed line equals the average counts from samples without spiking Stx2a plus three SD.
Figure 6:
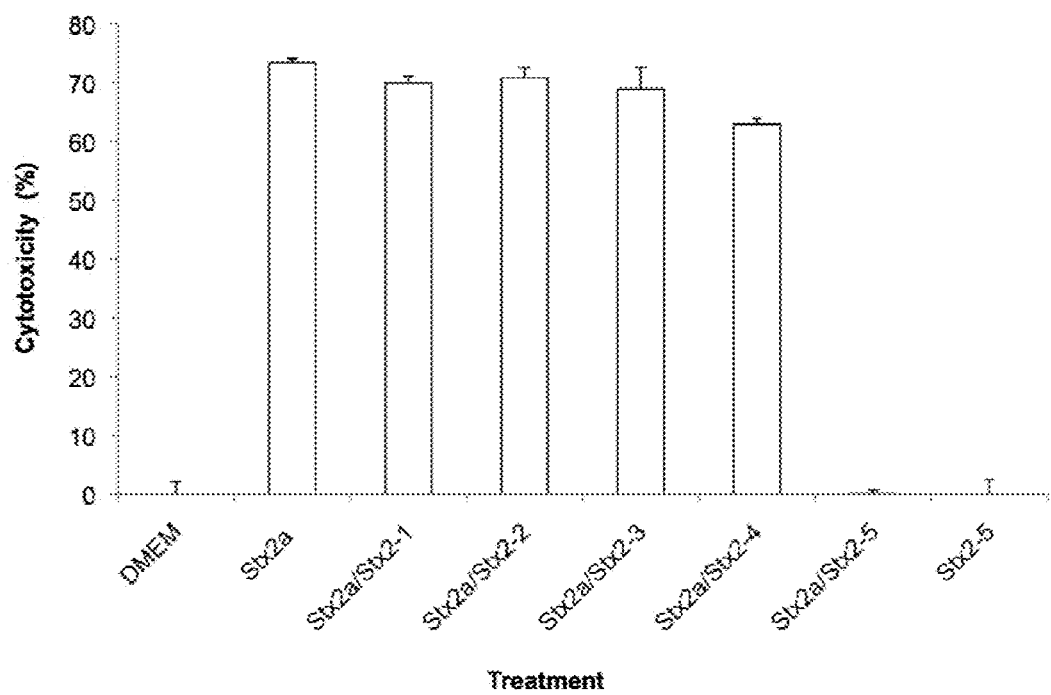
FIG. 6 is a plot of the neutralization of Stx2a cytotoxicity with mAbs. Vero cells were n incubated in DMEM medium containing Stx2a (10 ng/mL) with or without the presence of mAbs Stx2-1, Stx2-2, Stx2-3, Stx2-4, and Stx2-5. The cytotoxicity for cells was calculated as: [(cps from negative control−cps from samples treated)/cps from negative control]× 100. Cells grown in DMEM medium were used as a negative control. The data shown represent the mean±SD of three replicates from one representative experiment. Three individual experiments were performed.

In order to develop a sensitive assay for Stx2 detection, a sandwich ELISA was established. All possible combinations of mAb pairs were evaluated using each of the five mAbs as either the capture or detector antibody (pre-labeled with biotin). The data shown in FIG. 4 indicates that the best result was obtained when using mAb Stx2-1 as a capture antibody and biotinylated mAb Stx2-2 as a detector antibody. Significantly lower signals were observed using any of the other combinations of capture and detector antibody. Low or no counts were observed when the same mAb was used as both the capture and detector antibody except for mAbs Stx2-2 and Stx2-5, which was expected because these two antibodies bound to both the A- and B-subunit of Stx2a on the western blot (FIG. 2a). A sandwich ELISA incorporating biotinylated mAb Stx2-2 as a detector antibody and mAb Stx2-1 as a capture antibody was further studied. A linear standard curve with $R^2=1$ was observed using Stx2a at the range of 10 to 1,000 pg/mL (FIG. 5). The LOD was between 1 and 10 pg/mL for Stx2a in PBS buffer.

Detection of Stx2a in Milk

The sandwich ELISA established above was validated for detection of Stx2a in milk matrices. Undiluted milk (1 mL) was spiked with 10 µL of PBS containing varying amounts of Stx2a and analyzed directly. Results from the assay indicated that the LOD for Stx2a was between 1 pg/mL and 10 pg/mL in 2% milk and between 10 pg/mL and 100 pg/mL in whole milk. The recovery of Stx2a from milk samples spiked at 10, 100, 200, and 400 pg/mL is summarized in Table 3. In 2% milk the recovery ranged from 90-125%. In whole milk the recovery varied from 90-114%.

In Vitro Toxin Neutralization

To test the ability of the five mAbs in neutralization against the cytotoxicity of Stx2a, Vero cells (100 µL of $0.5 \times 10^5$ cells/mL) were seeded in wells of a clear 96-well tissue culture plate and incubated overnight. Cells were then treated with DMEM medium (as a negative control), Stx2a (10 ng/mL), mAb (20 µg/mL), and Stx2a (10 ng/mL)+each mAb (20 µg/mL), respectively. In the absence of mAbs, 73% of the toxin treated cells died within 24 hours at a dose of 10 ng/mL. In the presence of individual mAbs Stx2-1, Stx2-2, Stx2-3, and Stx2-4 the cytotoxicity measured was similar to the cells without adding mAb. However, cells treated with Stx2 in the presence of mAb Stx2-5 were totally protected from death and the cell survival rate was similar to the DMEM medium (no-toxin control). No toxicity was observed for cells treated with any individual mAb without the presence of the toxin.

Mouse In Vivo Neutralization of E. coli Shiga Toxin

Experimental Materials.

Stx2 toxin was purchased from List Biological Laboratories, Inc. (Campbell, Calif.). Toxin was reconstituted as suggested by manufacturer into a 100 ng/µL stock (in 50 mM Tris, 100 mM NaCl, 0.1% Trehalose), aliquoted and frozen at −80° C. until use. Monoclonal antibodies against Stx2 (Stx2-1, Stx2-2, Stx2-4, Stx2-5, and Stx2-6) were prepared as described (13). Briefly, antibodies were purified from ascites fluids and diluted in sterile phosphate buffered saline, pH 7.4 (PBS) into indicated doses. Female Swiss Webster mice of 4-5 weeks of age were purchased from Charles River (Portage, Mich.) and were fed ad libitum and housed in standard conditions. Mouse experiments were performed according to animal-use protocols approved by the Institutional Animal Care and Use Committee of the United States Department of Agriculture, Western Regional Research Center.

Determination of Mean Lethal Dose.

Groups of at least 10 randomly selected mice were treated by intraperitoneal (ip) injection with 500 µL per dose of serial dilutions of Stx2 (in a range that spans high lethality to no deaths). Mice were monitored for health or death for up to 14 days post-intoxication. The mean lethal dose ($LD_{50}$) was calculated by the Well and/or the Reed and Muench method (Weil, C. S., Biometrics, (1952) 8:249; Reed and Muench, Am J Hygiene (1938) 27:493-7).

Mouse Protection Assay.

Figure 12:
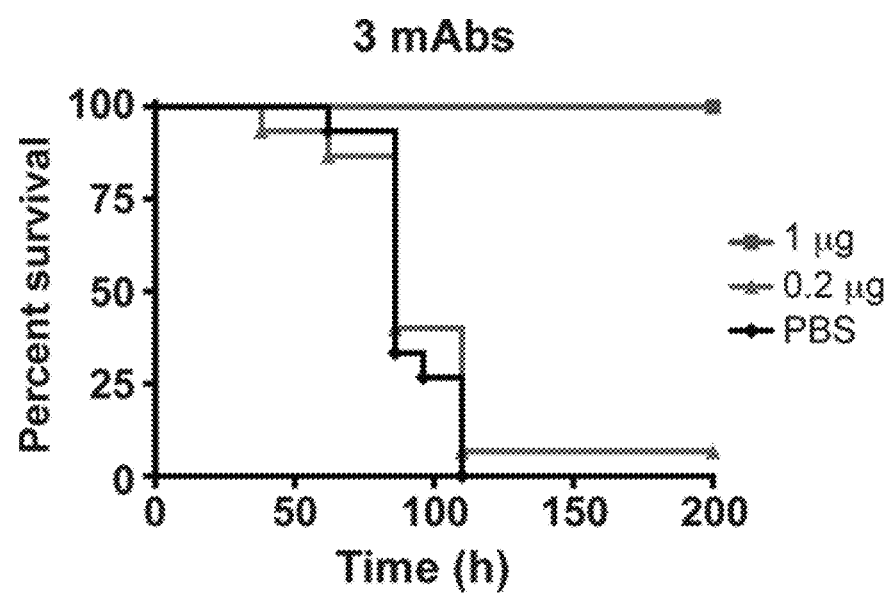
FIG. 12 is a graph of mice were treated with 100 µL of indicated doses (25, 5, 1 or 0.2 µg per mouse of individual mAbs or combination of mAbs (1:1:1 ratio of Stx2-1, Stx2-2 and Stx2-5).

Groups of at least 10 mice were treated with 100 µL of indicated doses (25, 5, 1 or 0.2 µg per mouse of individual mAbs or combination of mAbs 1:1:1 ratio of Stx2-1, Stx2-2 and Stx2-5) by tail vein injection (iv) about 30 min before iv administration with a 100 µL lethal dose (3 ip mouse $LD_{50}$ or 18 ng/mouse) of Stx2. Mice were monitored over 14 days. Survival curves (FIG. 12) were plotted using PRISM 6 (GraphPad Software, Inc. La Jolla, Calif.).

ELISA for Stx2.

ELISA was performed as described previously (He et al., J Immunol Methods, (2013) 389:18-28). Briefly, black NUNC plates were coated with mAb Stx2-1 (100 µL/well of a 5 µg/mL, solution in PBS) and incubated overnight at 4° C. Plates were then blocked by adding 300 µL of blocking buffer containing 3% bovine serum albumin (BSA) in 0.02 M Tris-buffered saline with 0.9% NaCl, pH 7.4 and 0.05% Tween-20 (TBST) and incubating for 1 hour at 37° C. Next, plates were washed twice with TBST. After toxin standards and samples (100 µL/well in PBS) were added, the plates were incubated for one hour at 37° C. and then washed six times with TBST. Next, a biotinylated detection antibody (mAb Stx2-2) was added (100 µL/well of a 100 ng/mL solution in blocking buffer). The plates were incubated for 1 hour at 37° C., washed six times with TBST and then 100 µL/well of 1:20,000 dilution of streptavidin-HRP (Invitrogen, Carlsbad, Calif.) in blocking buffer was added. The plates were incubated for 1 hour at 37° C. Finally, the plates were washed six times with TBST and SUPERSIGNAL West Pico Chemiluminescent Substrate (Pierce, Rockford, Ill.) was added. The limit of detection (LOD) was defined as the lowest toxin concentration at which the average ELISA reading was three standard deviations above the negative control.

Toxicokinetics of Stx2.

The biologic half-lives of Stx2 were determined in the presence or absence of mAbs against Stx2. Mice were treated iv with 100 ng per mouse (100 µL of 1,000 ng/ml stock) of Stx2. Blood from sets of at least 6 mice per time point were taken by submandibular bleeding (2, 5, 10, 20, 30 min and 1, 1.5, 2, 3, 6 and 8 h) into serum or plasma collectors (BD, San Jose, Calif.). Blood was incubated on ice for at least 1 h, centrifuged for 10 min at 3000×g to separate sera from cellular fractions. Sera were then aliquoted and frozen at −80° C. until use. Sera were also collected from untreated mice for use as untreated controls and pooled untreated mice sera and buffer was use to dilute Stx2 standards. In mAb clearance, a 100 µL sample of 90 µg/mL mAb combination (9 µs total mAb combination per mouse of 3 µg ea of Stx2-1, Stx2-2 and Stx2-5) in PBS buffer was administered iv 2 min after toxin. Blood samples were collected from sets of 3 mice at each time point (2, 5, 10, 20, 30 min and 1, and 2 h) as described above. The half-lives and concentration of unknown Stx2 was determined by comparing values determined by ELISA. The averages at each time point were plotted±standard error of the mean (SEM), with standard curves plotted in non-linear regression of the second polynomial (Prism 6). Averages of Stx2 values at 5 min and 1 h time in sera were compared with those in plasma with no statistically significantly difference in the sample values between plasma and sera.

Treatment of Mice Post-Intoxication or Pre-Intoxication with Stx2 mAbs.

For the simulation of post-intoxication model, mice were treated by iv with 100 µL of 18 ng of Stx2. At different time points after toxin injection (2, 5, 10, 20, 40 min after toxin), 100 µL per mouse of a combination of mAbs (9 µg/mouse or 3 µg ea of Stx2-1, Stx2-2 and Stx2-5 mAbs) were administered by iv. For pre-intoxication models, mice were treated by iv with 100 µL of the same Stx2 mAb combination at 3, 4, 5, 6, 7, and 8 weeks prior to iv treatment with 100 µL of 18 ng/mouse Stx2. Mice were then monitored for at least 14 days post-intoxication.

Detection of Stx2 in Mouse Serum.

Figure 7:
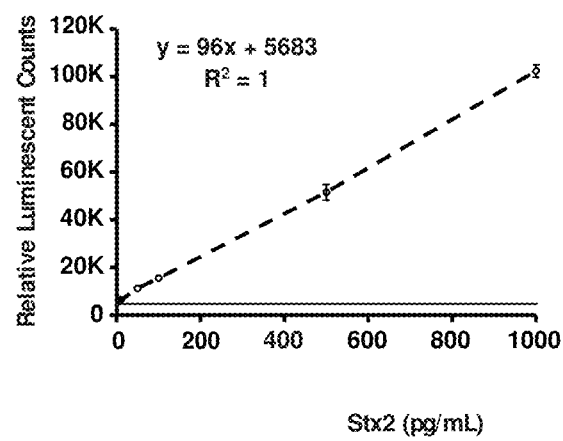
FIG. 7 is a graph of a standard curve of Stx2 spiked in mouse serum. Known standards ranging from 10-1,000 pg/ml of Stx2 in control sera (pooled healthy mouse sera) were used to determine the concentration of Stx2 in unknown blood samples.

Currently, diagnosis of STEC infection is determined primarily through isolation of the pathogen from stool culture. STEC strains are distinguished from *E. coli* strains comprising the normal intestinal flora based on chemical markers, such as the unique sorbitol negative fermentation property of the 0157 strain using isolation media (March and Ratnam, J Clin Microbiol, (1986) 23:869-72). However, this approach was unable to identify non-0157 STEC strains. To determine if a bacterial isolate is a STEC, the best way is to examine the production of Stxs. The availability of an assay that could detect Stxs in the blood system directly will greatly improve the identification of individuals at high risk of HUS during and after a STEC outbreak. Different formats of ELISAs for the detection of Stxs in sera samples were utilized and it was determined that the ELISA as embodied herein (He et al., J Immunol Methods, (2013) 389:18-28, was at least 10-fold more sensitive than other formats tested, LOD for Stx2 spiked in mouse sera was 10 pg/mL (FIG. 7). The linear quantification range of the assay is 10 to 10,000 pg/mL.

In Vivo Toxicity and Toxicokinetics of Stx2.

To determine the toxicity of Stx2 in vivo, we administered the toxin intraperitoneally to female Swiss Webster mice of 4-5 weeks of age. The mouse $LD_{50}$ of a commercially available Stx2 was determined as 290 ng/kg or about 6 ng per average sized mouse. Intoxication with Stx2 resulted in weight loss, frequent urination (observed as increased water intake and number of wet cages), and ultimately death. Mice that survived Stx2 challenge recovered weight, as well as normal urination behavior.

Figure 8:
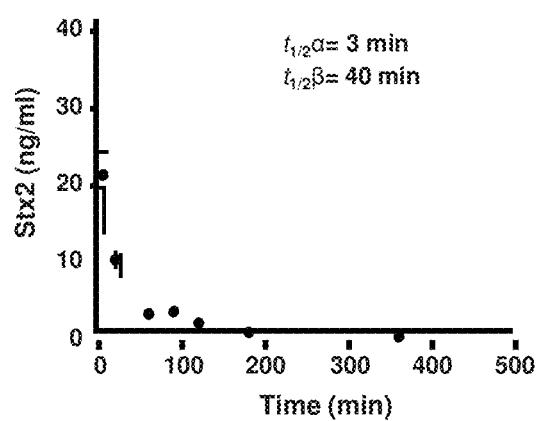
FIG. 8 is a graph of the biologic half-lives of Stx2 in mouse serum. Stx2 was introduced into mice by iv. Sera was taken and Stx2 concentration was determined at 2, 5, 10, 20, 30 min and 1, 1.5, 2, 3, 6 and 8 h after intoxication. The fast distribution phase t1/2 α and slow clearance phase t1/2 β were determined based on standard curves plotted in non-linear regression of the second polynomial (Prism 6).

Little is known thus far about the in vivo toxicokinetics of Stx2. Using the sensitive assay described above, detection of minute amounts of Stx2 in animal sera are achieved. Mice treated with 100 ng/mouse of Stx2 via iv were bled and sacrificed over time (2, 5, 10, 20, 30 min and 1, 1.5, 2, 3, 6 and 8 h at n≥5 per time point). The concentration of unknown samples was determined by ELISA using a standard curve of known samples diluted in pooled mouse sera. The half-lives, consisting of the distribution phase ($t_{1/2}$ α) and the slower clearance phase ($t_{1/2}$ β) were determined as 3 min and 40 min, respectively (FIG. 8), with no statistically significant difference between the concentrations of Stx2 recovered from sera or plasma.

Protection of Mice from Stx2 with Monoclonal Antibodies.

Figure 9:
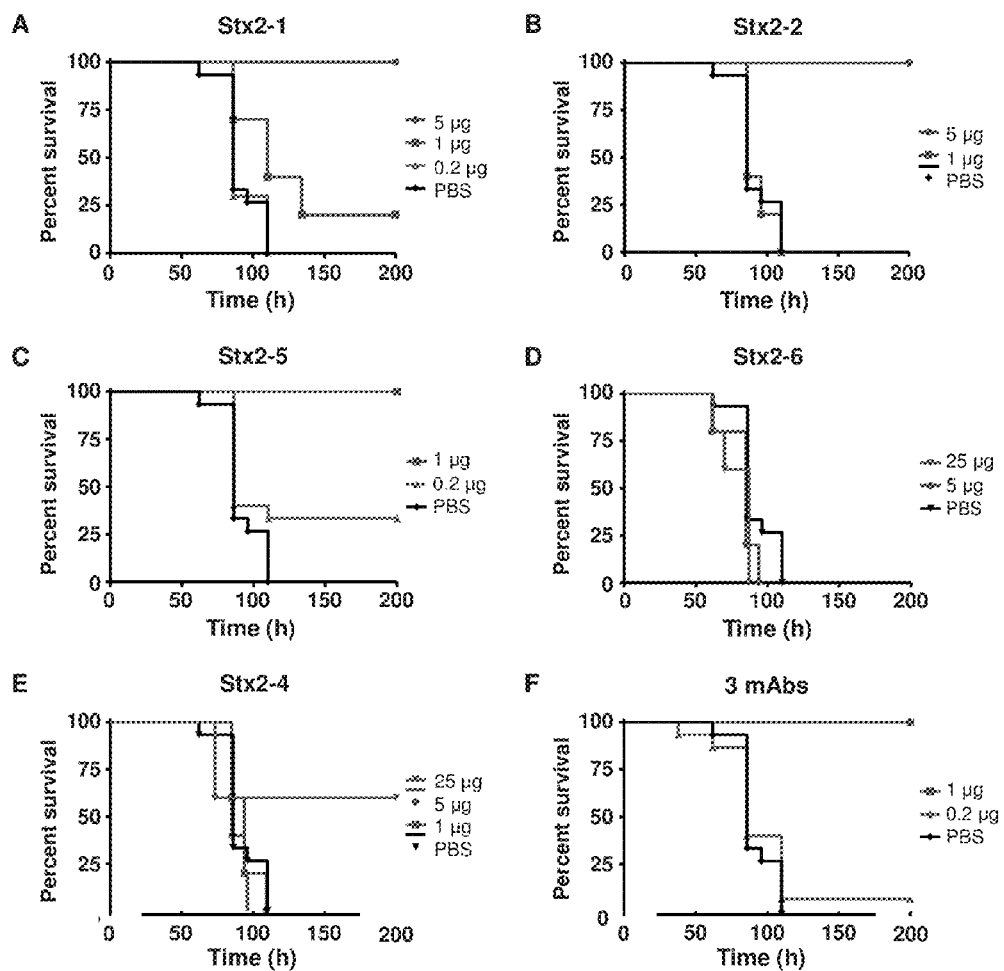
FIG. 9A-F are graphs of monoclonal antibody protection of mice from Stx2. Mice (N≥10) were treated with different doses of single and combination of anti-Stx2 mAbs (A. Stx2-1; B. Stx2-2; C. Stx2-5; D. Stx2-6; E. Stx2-4 and F. 3 mAbs, 1:1:1 of Stx2-1, Stx2-2, and Stx2-5) about 30 min prior to administration with a lethal dose (3 ip mouse LD50) of Stx2. The percentage of survival of mice was plotted over time. Control mice were treated with sterile PBS instead of mAb.

The mAbs as described herein were tested for the in vivo neutralization of Stx2. Mice were treated with different doses of a single mAb or a 1:1:1 combination of anti-Stx2 mAbs (Stx2-1, Stx2-2, and Stx2-5) about 30 min prior to administration with a lethal dose (3 ip mouse $LD_{50}$) of Stx2. The survival of mice treated with mAbs or sterile PBS were plotted over time (FIG. 7). In contrast to the Vero cell toxin neutralization assays, mAbs Stx2-1 and Stx2-2 protected mice well, providing complete protection from death with only 5 jug/mouse of mAbs (FIGS. 9A and 9B). MAb Stx2-5 provided the highest level of protection, showing full protection at 1 µg/mouse (FIG. 9C). MAbs Stx2-4 and Stx2-6 did not provide significant protection from Stx2 even at 25 µg mAb/mouse indicating that the protective effect seen with mAbs Stx2-1, 2 and 5 were not due to the general presence of mAbs (FIGS. 9D and 9E).

Figure 10:
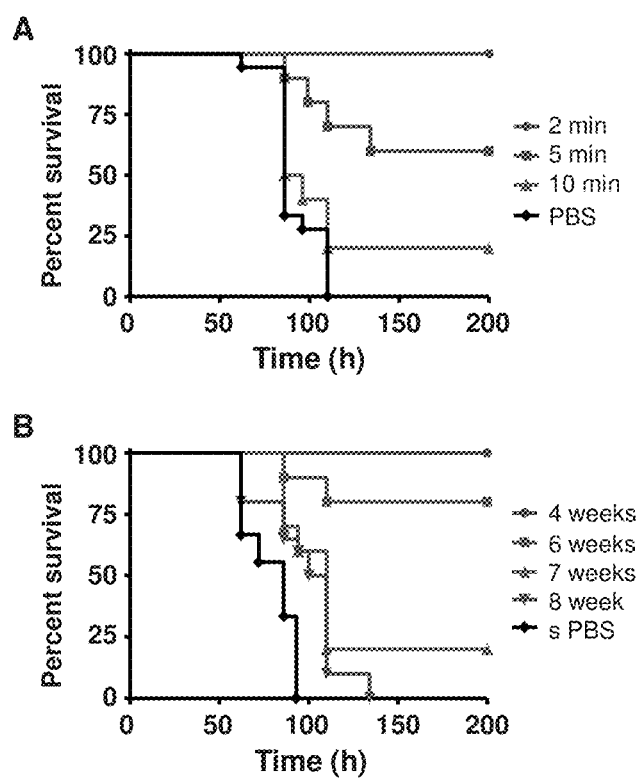
FIGS. 10A and B are graphs of the survival of mice treated with mAbs before and after Stx2 intoxication. A. Mice were treated with a lethal dose of Stx2 followed by treatment with a mAb combination against Stx2 at 2, 5, 10, 20, 30 min and 1 h. B. Mice were treated with a combination of mAbs against Stx2 at 4, 5, 6, 7, 8 weeks before injection with Stx2.

Other studies with antibody protection against toxins have shown a substantial additive protective effect of combining two or more mAbs (5, 23). In this study, a combination of the best protective mAbs Stx2-1, Stx2-2 and Stx2-5 did give complete protection from Stx2 at 1 µg mAb/mouse (FIG. 10F).

Survival of Mice Treated with mAbs Before and after Intoxication with Stx2.

To elucidate the effective time window of neutralizing mAbs for protection relative to intoxication, we investigated the efficacy of mAbs before and after toxin exposure. Mice were treated by iv with a combination of mAbs against Stx2 (3 µg each of mAbs Stx2-1, Stx2-2, and Stx2-5) at 2, 5, 10, 20 and 40 min after injection. Mice treated with mAbs after intoxication conferred some degree of protection as shown by the increase of time-to-death (FIG. 10A). All mice treated with mAbs at 2 min post intoxication (mpi) survived; 60% and 20% of mice survived when treated at 5 and 10 mpi, respectively. All control mice that were treated with PBS instead of mAbs died within 5 days after intoxication (FIG. 10A). Significant protection was observed when mAbs were administrated before toxin exposure. Mice were treated with the same combination of mAbs at weeks 4 to 8 before injection with a lethal dose of Stx2 (18 ng/mouse by iv). All mice survived when treated with mAbs 4 weeks before intoxication while 80% of mice treated with mAbs at 5 and 6 weeks before intoxication survived (FIG. 10B and data not shown). Even mice treated with mAbs 7 weeks before intoxication displayed a protective effect as shown by the 20% survival with a slight increase in the median survival from 86 h in the PBS control to 110 h (FIG. 10B).

Clearance of Stx2 by Monoclonal Antibodies.

Figure 11:
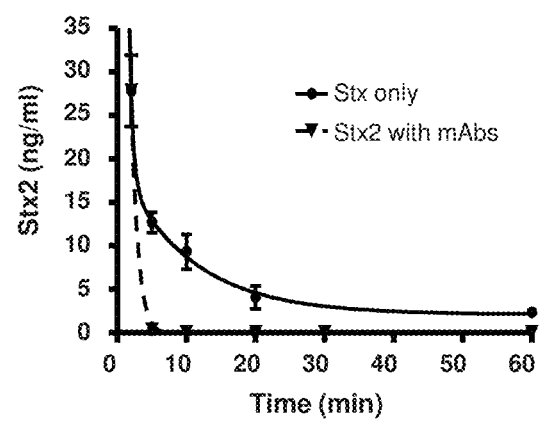

To test whether the protection of mice from Stx2 by antibodies is due to the rapid serum clearance of the toxin, we examined the toxicokinetics of Stx2 in the presence or absence of mAbs. Mice were injected with Stx2 by iv, followed by iv introduction of the 3 mAbs combination (Stx2-1, Stx2-2, and Stx2-5) after two min. Sera were obtained at 2, 5, 10, 20, 30 min and 1 h, and 2 h and the concentration of Stx2 at each time point was determined using the method described above. Within 3 mpi, the circulating titer of Stx2 went from 13±1.2 ng/mL in the no mAb control to 0.3±0.05 ng/mL when mAbs were added (FIG. 11); and at 8 mpi, Stx2 went from 9.3±1.2 ng/mL in non treated animals to 8±3 pg/mL in mAb-treated animals, suggesting that this combination of mAbs protected mice from Stx2 intoxication through accelerating the clearance of toxin from the bloodstream.

---

What is claimed is:

1. A monoclonal antibody produced by a continuous hybridoma cell line selected from the group consisting of deposit accession number PTA-13614 and PTA-13615.

2. A composition comprising the monoclonal antibody of claim 1.

3. A method for detecting Shiga toxin 2 and variants thereof comprising (1) incubating a sample with the monoclonal antibody produced by a continuous hybridoma selected from the group consisting of deposit accession number PTA-13614 and PTA-13615, and mixtures thereof; and (2) detecting the antibody-Shiga toxin 2 complex wherein the presence or absence of the complex indicates the presence or absence of Shiga toxin 2 in the sample.

4. A kit for detecting Shiga toxin 2 in a sample, said kit comprising; (1) a container comprising a monoclonal antibody produced by a continuous hybridoma selected from the group consisting of deposit accession number PTA-13614 and PTA-13615, and mixtures thereof: and (2) instructions for using the antibody for the purpose of binding to Shiga toxin 2 to form, an immunological complex and detecting the formation of the immunological complex suck that presence or absence of immunological complex correlates with presence or absence of Shiga toxin 2 in said sample.

5. A method for detecting Shiga toxin 2 according to claim 3, wherein said sample is aqueous, biological, environmental or a food product.

6. A method for capturing Shiga toxin 2 from a sample, said method comprising contacting said sample with a monoclonal antibody of claim 1 and isolating the complex formed between the Shiga toxin 2 in the sample and the monoclonal antibody.

* * * * *